United States Patent [19]

Toldy et al.

[11] 4,369,325

[45] Jan. 18, 1983

[54] 1,3-DIARYL-2-IMINO-IMIDAZOLIDINES AND COMPOUNDS

[75] Inventors: Lajos Toldy; Zoltán Zubovics; Mariann Kürti; Inge Schäfer, all of Budapest, Hungary

[73] Assignee: EGYT Gyógyszervegyészeti Gyár, Budapest, Hungary

[21] Appl. No.: 292,002

[22] Filed: Aug. 11, 1981

Related U.S. Application Data

[62] Division of Ser. No. 30,149, Apr. 16, 1979, Pat. No. 4,284,642.

[30] Foreign Application Priority Data

Apr. 21, 1978 [HU] Hungary .................... GO-1400

[51] Int. Cl.³ .................. C07D 233/44; C07D 233/48
[52] U.S. Cl. ..................................................... 548/315
[58] Field of Search ........................................ 548/315

[56] References Cited

PUBLICATIONS

Wanzlick et al., "Berichte", vol. 98, (1965), pp. 3170–3177.

*Primary Examiner*—Robert W. Ramsuer
*Attorney, Agent, or Firm*—Ernest F. Marmorek

[57] ABSTRACT

A compound of the general formula (I),

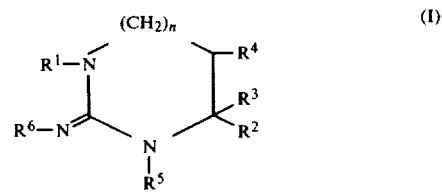

is described wherein $R^1$ and $R^5$ each represent a phenyl group optionally substituted with 1 to 3 lower alkoxy, halo, lower alkyl, monohalo-(lower)-alkyl, dihalo-(lower)-alkyl and/or trihalo-(lower)-alkyl groups, $R^2$ stands for hydrogen or a lower alkyl group optionally substituted with a hydroxy group or 1 to 3 halogen atoms, $R^3$ and $R^4$ each represent a hydrogen atom or a lower alkyl group, and $R^6$ stands for a carbamoyl, thiocarbamoyl or amidino group having optionally one or two lower alkyl and/or lower alkoxycarbonyl substitutes, or a group of the general formula $R^7$-CO-wherein $R^7$ stands for a lower analkoxy group, an aryloxy group, or an aralkoxy group, and n is equal to 0, provided that when $R^1$ and $R^5$ each represent a phenyl group, $R^2$and $R^3$ may not stand for hydrogen or a pharmaceutically acceptable acid addition salt, a pure isomer or an isomeric mixture thereof. The compounds posses antiphlogistic and diuretic activity.

4 Claims, No Drawings

1,3-DIARYL-2-IMINO-IMIDAZOLIDINES AND COMPOUNDS

This is a division, of application Ser. No. 30,149, filed on Apr. 16, 1979 now U.S. Pat. No. 4,284,642.

The invention relates to new substituted 1,3-diaryl-2-imino-imidazolidines and 2-imino-hexahydro-pyrimidines and pharmaceutical compositions containing the same, as well as to a process for the preparation thereof.

The new compounds according to the invention correspond to the general formula (I),

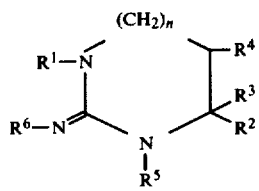

wherein $R^1$ and $R^5$ each represent a phenyl group optionally substituted with 1 to 3 lower alkoxy, halo, lower alkyl, monohalo-(lower)-alkyl, dihalo-(lower)-alkyl and/or trihalo-(lower)-alkyl groups, $R^2$ stands for hydrogen, formyl group, carboxy group, lower alkoxycarbonyl group, hydroxy-(lower)-alkoxycarbonyl group, or a lower alkyl group optionally substituted with a hydroxy group, 1 to 3 halogen atoms, a lower alkoxy group, a lower alkanoyloxy group, a lower alkylsulfonyloxy group, an arylsulfonyloxy group, a free or etherified mercapto group, a cyano group, a nitro group, an unsubstituted or substituted amino group or a group of the general formula —CO—Y, wherein the etherified mercapto group is a group derived from a lower alkylmercaptan having optionally a mono- or di-(lower alkyl)-amino substituent, a mercapto-(lower)-alkanecarboxylic acid having optionally an amino substituent or a 3 to 7-membered heterocyclic compound containing 1 to 4 nitrogen, sulfur and/or oxygen atoms in the ring and having a mercapto substituent, the substituted amino group is a group having one or two identical or different lower alkyl substituents or a $C_{2-6}$ α,ω-alkylene substituent containing optionally a further hetero atom, such as nitrogen, sulfur or oxygen atom, in the carbon chain, and Y stands for hydroxy, amino, lower alkoxy or hydroxy-(lower)-alkoxy group, $R^3$ and $R^4$ each represent hydrogen atom or a lower alkyl group, or $R^2$ and $R^3$ form together an oxo or a methylene group, $R^6$ stands for hydrogen atom, cyano group, a lower alkyl group optionally substituted with 1 to 3 halogen atoms, hydroxy groups, carboxy groups or lower alkoxycarbonyl groups, a carbamoyl, thiocarbamoyl or amidino group having optionally one or two lower alkyl and/or lower alkoxycarbonyl substituents, or a group of the general formula $R^7$—CO— or $R^8$—$SO_2$—, wherein $R^7$ stands for hydrogen, a lower alkyl group having optionally 1 to 3 halogen substituents, a lower alkoxy group, an aryloxy group, an aralkoxy group, a phenyl group having optionally a halogen or lower alkyl substituent, or a mono- or polycyclic cycloalkyl group of up to 10 carbon atoms, and $R^8$ represents a phenyl group having optionally a lower alkyl substituent, and n is equal to 0 or 1, with the proviso that when $R^1$ and $R^5$ each represent a phenyl group and n is equal to zero, $R^2$ and $R^3$ may not stand for hydrogen and they may not form together an oxo group, either.

The compounds of the general formula (I) may appear in the form of various isomers and isomeric mixtures. All of the possible isomers and mixtures thereof are embraced by the scope of the invention.

The scope of the invention also embraces the pharmaceutically acceptable acid addition salts of the compounds having the general formula (I), furthermore their complexes formed with inorganic salts.

The lower alkyl and lower alkoxy groups mentioned above are those containing 1 to 5 carbon atoms, whereas the lower acyloxy groups may contain 2 to 5 carbon atoms. All of these carbon chains may be straight or branched. The term "halo" includes iodine, bromine, chlorine and fluorine atoms.

Based on the above, in the compounds of the general formula (I)

$R^1$ and $R^5$ each may stand for e.g. phenyl, 2,6-dimethylphenyl, 2,3-dimethylphenyl, 2,4,6-trimethylphenyl, 2-chloro-6-methylphenyl, 3-trifluoromethylphenyl, 4-chlorophenyl, 4-methoxyphenyl, 2,6-diethylphenyl or 2,6-dichlorophenyl group, $R^2$ may represent e.g. hydrogen atom or a methyl, n-butyl, hydroxymethyl, mercaptomethyl, fluoromethyl, chloromethyl, bromomethyl, iodomethyl, trifluoromethyl, trichloromethyl, methoxymethyl, methylmercaptomethyl, carboxymethyl-mercapto-methyl, (β-diethylaminoethyl)-mercapto-methyl, 2-thienyl-mercaptomethyl, aminomethyl, 2-aminoethyl, diethylaminomethyl-morpholinomethyl, cyanomethyl, carboxamidomethyl, carboxymethyl, ethoxycarbonylmethyl, (β-hydroxy-ethoxy)-carbonylmethyl, nitromethyl, carboxy, methoxycarbonyl, (β-hydroxyethoxy)-carbonyl or formyl group, $R^3$ and $R^4$ each may stand for e.g. hydrogen or a methyl group, and $R^6$ may represent e.g. hydrogen atom or a cyano, methyl, 2,2,2-trifluoroethyl, n-butyl, formyl, acetyl, trifluoroacetyl, benzoyl, p-chlorobenzoyl, 1-adamantyl-carbonyl, benzenesulfonyl, p-toluenesulfonyl, methoxycarbonyl, ethoxycarbonyl, tert.-butoxycarbonyl, phenoxycarbonyl, benzyloxycarbonyl optionally substituted on the aromatic ring by one or two halogen atoms, lower alkyl and/or lower alkoxy groups, carboxymethyl, ethoxycarbonylmethyl, β-hydroxyethyl, carboxamido, N-methyl-carboxamido, N-(ethoxycarbonyl)-carboxamido, thiocarbamoyl, N-(ethoxycarbonyl)-thiocarbamoyl, amidino, N-(ethoxycarbonyl)-amidino or $N^1$-(ethoxycarbonyl)-$N^2$-methyl-amidino group.

Only three compounds are described in the literature which are structurally related to the new compounds of the general formula (I). One of them is 1,3-diphenyl-2-imino-imidazolidine, which is prepared by reacting phenylcyanamide with 1,2-dibromoethane and subjecting the resulting ethylene-bis-phenyl-cyanamide to partial hydrolysis and spontaneous cyclization (see Traube and Wedekind: Ber. 33, 1385 /1900/), or by subjecting the respective 2,2'-bis(1",3"-diphenyl)-imidazolidinium-halides to alkaline splitting (see Wanzlick et al.: Ber. 98, 3170 /1965/). The two other known compounds belong to the 4-oxo-imidazolidines. These compounds, i.e. 1,3-diphenyl-2-imino-4-oxo-imidazolidine and 1-phenyl-2-imino-3-(p-nitrophenyl)-4-oxo-imidazolidine, are prepared by reacting a metal salt of an aryl-cyanamide with the appropriately substituted chloroacetanilide (see U.S. Pat. No. 2,557,911; Hoegberg and Adams: J. Am. Chem. Soc. 73, 2942 /1951/).

These two latter compounds are referred to in the literature as bactericidal agents, whereas no biological activity is assigned to the first compound.

Now it has been found that the new compounds of the general formula (I), furthermore their pharmaceutically acceptable acid addition salts and complexes formed with inorganic salts exert valuable diuretic and antiphlogistic effects.

The new compounds of the invention can be prepared as follows:

(a) a compound of the general formula (II),

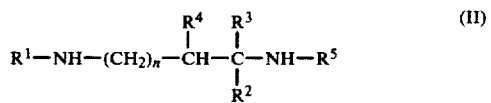

wherein $R^1$, $R^2$, $R^3$, $R^4$, $R^5$ and n are as defined above, is reacted with a cyanogen halide to obtain a compound of the general formula (I), wherein $R^1$, $R^2$, $R^3$, $R^4$, $R^5$ and n are as defined above and $R^6$ is hydrogen, in the form of its hydrohalide, or (b) a compound of the general formula (III),

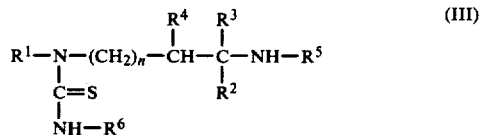

wherein $R^1$, $R^2$, $R^3$, $R^4$, $R^5$ and n are as defined above and $R^6$ stands for hydrogen or a lower alkyl group, is subjected to ring closure by desulfuration with a heavy metal oxide, or (c) a compound of the general formula (IV),

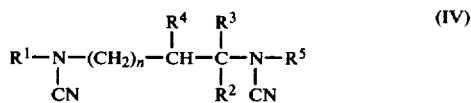

wherein $R^1$, $R^2$, $R^3$, $R^4$, $R^5$ and n are as defined above, is subjected to partial hydrolysis coupled with spontaneous ring closure to form a compound of the general formula (I), wherein $R^6$ stands for hydrogen and $R^1$, $R^2$, $R^3$, $R^4$, $R^5$ and n have the same meanings as defined above, with the proviso that $R^1$ and $R^5$ are always the same, or (d) a compound of the general formula (V),

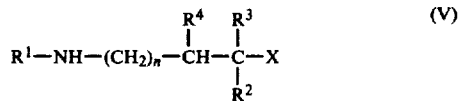

wherein $R^1$, $R^2$, $R^3$, $R^4$ and n are as defined above and X is halo, is reacted with a cyanamide of the general formula $R^5$—NH—CN, wherein $R^5$ is as defined above, and, if desired, a compound of the general formula (I) is converted into another compound of the general formula (I) by methods known per se, and/or, if desired, a free base of the general formula (I) is liberated from its salts, and/or, if desired, a free base of the general formula (I) is converted into its acid addition salt or complex formed with an inorganic salt, and/or, if desired, the individual isomer of the product are separated from each other.

According to a particularly preferred variant of method (a) a compound of the general formula (II), wherein $R^1$, $R^2$, $R^3$, $R^4$, $R^5$ and n are as defined above, is reacted with 1.0 to 3.0 moles of a cyano halide, calculated for 1 mole of the starting substance, in an appropriate solvent, such as ethanol, n-propanol, isopropanol, n-butanol, benzene, toluene, xylene or chlorobenzene, at a temperature between room temperature and the boiling point of the reaction mixture, preferably at about 80° C. to 130° C.

The starting substances of the general formula (II) are in part known from the literature (see e.g. L. Shapiro et al.: J. Am. Chem. Soc. 80, 3734 /1958/; U.S. patent specification No. 2,993,831; I. K. Lewis et al.: J. Org. Chem. 29, 1183 /1964/; A. E. Schouten: Rec. trav. chim. 56, 541 /1937/; R. Daniels and B. D. Martin: J. Org. Chem. 27, 178 /1962/; A. F. McKay and E. J. Tarlton: J. Am. Chem. Soc. 74, 2978 /1959/), or can be prepared according to methods known per se.

Method (b) of the process of the invention is performed preferably so that a compound of the general formula (III), wherein $R^1$, $R^2$, $R^3$, $R^4$, $R^5$ and n are as defined above and $R^6$ stands for hydrogen or a lower alkyl group, is reacted with a heavy metal oxide, such as mercury(II)oxide or lead(II)oxide, in an inert solvent, such as toluene, xylene or chlorobenzene, at a temperature of about 80° C. to 140° C.

The starting substances of the general formula (III) can be prepared by methods known per se (see e.g. published German patent application No. 2,140,405; D. T. Elmore and J. R. Ogle: J. Chem. Soc. 1958, 1141).

According to a preferred variant of method (c) of the invention the compounds of the general formula (IV), wherein $R^1$, $R^2$, $R^3$, $R^4$, $R^5$ and n are as defined above and $R^1$ and $R^5$ are always the same, are subjected to partial hydrolysis under the conditions applied by Traube and Wedekind (loc. cit.), whereupon a spontaneous cyclization also takes place. In this way compounds of the general formula (I), wherein $R^1$, $R^2$, $R^3$, $R^4$, $R^5$ and n are as defined above, $R^1$ and $R^5$ are always the same and $R^6$ stands for hydrogen, are obtained.

The starting substances of the general formulae (IV) are prepared by methods known per se (see Traube and Wedekind, loc. cit.).

Method (d) of the invention is performed preferably so that a compound of the general formula (V), wherein $R^1$, $R^2$, $R^3$, $R^4$, n and X are as defined above, is reacted with a cyanamide of the general formula $R^5$—NH—CN, wherein $R^5$ is as defined above, at a temperature between about room temperature and 100° C., either in a solvent-free medium or in the presence of a solvent, such as benzene, toluene, xylene, dimethylformamide or dimethylsulfoxide, in the optional presence of a base, such as sodium methoxide, sodium ethoxide or potassium tert.-butoxide. This method yields compounds of the general formula (I), wherein $R^1$, $R^2$, $R^3$, $R^4$, $R^5$ and n are as defined above and $R^6$ stands for hydrogen.

Those compounds of the general formula (I), wherein $R^6$ is a lower alkyl group having optionally 1 to 3 nalo, hydroxy or lower alkoxycarbonyl substituents, are prepared according to the invention by reacting a compound of the general formula (I), wherein $R^1$, $R^2$, $R^3$, $R^4$, $R^5$ are n are as defined above and $R^6$ stands for hydrogen, with a compound of the general formula $R^6$-Z, wherein $R^6$ is as defined in this paragraph and Z represents a halogen atom, preferably chlorine, bromine or iodine atom, or a group of the general formula $R^9$—$SO_2O$—, wherein $R^9$ is a lower alkyl group having optionally 1 to 3 halogen substituents, preferably a trichloromethyl group. The reaction is performed in an appropriate solvent, such as acetone, methyl-ethyl-ketone, acetonitrile, dimethylformamide, hexamethylphosphoric triamide, benzene, toluene, or xylene, in the presence of a base, such as sodium or potassium carbonate or sodium or potassium hydrocarbonate, at a temperature between about room temperature and 150° C. If desired, the excess of the starting substance can also be applied as acid-binding base in the above reaction.

Those compounds of the general formula (I), wherein $R^6$ stands for a group of the general formula $R^7$—CO— or $R^8$—$SO_2$— and $R^1$, $R^2$, $R^3$, $R^4$, $R^5$, $R^7$, $R^8$ and n are as defined above, are prepared according to the invention by reacting a compound of the general formula (I), wherein $R^6$ stands for hydrogen, with a compound of the general formula $R^7$—CO—Z or $R^8$—$SO_2$—Z, wherein $R^7$, $R^8$ and Z are as defined above. The reaction is performed in an appropriate solvent, such as chloroform, 1,2-dichloroethane or pyridine, at a temperature between about 0° C. and 100° C., in the presence of an acid binding agent, such as a base (e.g. triethylamine) of an excess of the starting substance itself.

Those compounds of the general formula (I), wherein $R^6$ stands for a thiocarbamoyl group having a lower alkyl or lower alkoxycarbonyl substituent, are prepared according to the invention by reacting a compound of the general formula (I), wherein $R^6$ stands for hydrogen, with the respective isothiocyanate. The reaction is performed in an appropriate solvent, such as chloroform, 1,2-dichloroethane or acetone, at a temperature between about room temperature and 80° C. If desired, the resulting compound can be reacted with methyl iodide in acetone, dimethylformamide or dimethylsulfoxide at a temperature between about 0° C. and 100° C. to obtain the respective S-methyl-isothiourea derivative. This latter compound can be reacted, if desired, with ammonia or a primary or secondary amine at a temperature between about 50° C. and 250° C. to form the respective guanidine compound.

Those compounds of the general formula (I), wherein $R^1$, $R^3$, $R^4$, $R^5$, $R^6$ and n are as defined above and $R^2$ stands for formyl group, can be prepared by oxidizing a compound of the general formula (I), wherein $R^2$ is hydroxymethyl, $R^1$, $R^3$, $R^4$, $R^5$ and n are as defined above and $R^6$ stands for a group of the general formula $R^7$—CO— wherein $R^7$ is as defined above, with an appropriate oxidizing agent, such as manganese dioxide or barium manganate, at a temperature between about room temperature and 100° C. and in a solvent medium, such as benzene, toluene, xylene, chloroform, 1,2-dichloroethane or acetonitrile, and, if necessary, splitting off the $R^7$—CO— group of the resulting product by treating it with an acid, such as a mineral acid (e.g. hydrochloric acid or sulfuric acid) or an organic acid (e.g. citric acid fumaric acid or maleic acid) in water or a lower aliphatic alcohol or in a mixture of these solvents at a temperature between about room temperature and 120° C.

If a compound of the general formula (I), wherein $R^1$, $R^3$, $R^4$, $R^5$, $R^6$ and n are as defined above and $R^2$ stands for carboxy group, is to be prepared, a compound of the general formula (I), wherein $R^2$ is hydroxymethyl, $R^6$ is a group of the general formula $R^7$—CO— and $R^1$, $R^3$, $R^4$, $R^5$, $R^7$ and n are as defined above, is oxidized, preferably with potassium permanganate, in an appropriate solvent, such as dioxane, tetrahydrofuran, diethyleneglycol dimethyl ether, water or a mixture thereof, in the presence of a base, such as sodium or potassium hydroxide, at a temperature between 0° C. and 50° C. If necessary, the $R^7$—CO— group of the resulting substance can be split off as described in the previous paragraph. If desired, the resulting acids can be converted into their esters by reacting them with an excess of a lower aliphatic mono- or polyol at a temperature between about 0° C. and 100° C. in the presence of an acid, preferably dry hydrochloric acid.

Those compounds of the general formula (I), wherein $R^1$, $R^3$, $R^4$, $R^5$, $R^6$ and n are as defined above and $R^2$ stands for a lower alkyl group having a lower alkoxy substituent, can be prepared by reacting a compound of the general formula (I), wherein $R^2$ is hydroxy-(lower)-alkyl group, $R^6$ is a group of the general formula $R^7$—CO—, and $R^1$, $R^3$, $R^4$, $R^5$, $R^7$ and n are as defined above, with a lower alkyl halide in an appropriate solvent, such as acetone, methyl-ethyl-ketone, dimethylformamide or dimethylsulfoxide, in the presence of an inorganic base, such as sodium hydride, potassium tert-.butoxide or silver oxide. If desired, the $R^7$—CO— group of the resulting compound can be split off as described above.

If a compound of the general formula (I), wherein $R^2$ is a lower alkyl group having a lower acyloxy substituent, $R^6$ is a group of the general formula $R^7$—CO—, and $R^1$, $R^3$, $R^4$, $R^5$, $R^7$ and n are as defined above, is to be prepared, a compound of the general formula (I), wherein $R^2$ is hydroxy-(lower)-alkyl, $R^6$ stands for hydrogen, and $R^1$, $R^3$, $R^4$, $R^5$ and n are as defined above, is reacted with an excess of a lower alkanecarboxylic anhydride at a temperature of 100° C. to 150° C. In the resulting compound the acyl group contained in $R^2$ is the same as that represented by $R^6$. If desired, the resulting compound can be treated with potassium or sodium hydroxide at room temperature in a solvent, such as methanol, ethanol, water or mixtures thereof, whereupon the acyl substituent of $R^2$ is split off selectively, and a compound of the general formula (I), wherein $R^2$ is hydroxy-(lower)-alkyl, $R^6$ is a group of the general formula $R^7$—CO—, and $R^1$, $R^3$, $R^4$, $R^5$, $R^7$ and n are as defined above, is obtained.

Those compounds of the general formula (I), wherein $R^2$ is a lower alkyl group having a lower acyloxy substituent, $R^6$ is hydrogen and $R^1$, $R^3$, $R^5$ and n are as defined above, can be prepared by reacting the hydrohalide of a compound of the general formula (I), wherein $R^2$ is hydroxy-(lower)-alkyl, $R^6$ is hydrogen, and $R^1$, $R^3$, $R^4$, $R^5$ and n are as defined above, with the respective acyl chloride in an appropriate solvent, such as dimethylformamide, dimethylsulfoxide or hexamethylphosphoric triamide, at a temperature of $-20°$ C. to $+50°$ C.

If a compound of the general formula (I), wherein $R^2$ is halo-(lower)-alkyl, is to be prepared, a compound of the general formula (I), wherein $R^2$ is hydroxy-(lower)-alkyl, $R^6$ is a group of the general formula $R^7$—CO—, and $R^1$, $R^3$, $R^4$, $R^5$, $R^7$ and n are as defined above, is reacted with an appropriate halogenating agent, such as thionyl chloride, phosphorus pentachloride, chloromethylene-dimethyl-ammonium chloride, bromomethylene-dimethyl-ammonium bromide, triphenylphosphine dibromide or triphenylphosphine diiodide, in a solvent, such as benzene, toluene, xylene, chloroform, 1,2-dichloroethane, acetonitrile or dimethylformamide, at a temperature between room temperature and the boiling point of the reaction mixture. The reaction can be performed optionally in the presence of a catalyst, such as dimethylformamide. If desired, the $R^7$—CO— group of the resulting compound is split off as described above.

Those compounds of the general formula (I), wherein $R^2$ is a halo-(lower)-alkyl group, preferably a chloro-(lower)-alkyl group, $R^6$ is a group of the general formula $R^7$—CO—, and $R^1$, $R^3$, $R^4$, $R^5$, $R^7$ and n are as defined above, can be reacted with an alkali halide, such as sodium or potassium bromide or iodide, in an appropriate solvent, such as a lower aliphatic alcohol (e.g. methanol, ethanol or isopropanol), dimethylformamide, dimethylsulfoxide or hexamethylphosphoric triamide, at a temperature of about 0° C. to 150° C. In this reaction the halogen atom present in substituent $R^2$ is replaced by an other halogen atom, such as a chlorine atom is replaced by a bromine or iodine atom. If desired, the $R^7$—CO— group of the resulting compound can be split off as described above.

Those compounds of the general formula (I), wherein $R^2$ is a lower alkyl group having a free or etherified mercapto substituent, are prepared by reacting a compound of the general formula (I), wherein $R^2$ is halo-(lower)-alkyl, $R^1$, $R^3$, $R^4$, $R^5$ and n are as defined above, and $R^6$ represents preferably a group of the general formula $R^7$—CO—, wherein $R^7$ is as defined above, with an alkali thiobenzoate, such as sodium or potassium thiobenzoate, in a solvent, such as acetone or methyl-ethyl-ketone, at a temperature between about room temperature and 80° C. The benzoyl group of the resulting S-benzoyl derivative is split off by treatment with a base, such as sodium methoxide or sodium ethoxide, in a lower aliphatic alcohol as solvent to obtain the respective mercapto compounds. If desired, the $R^7$—CO— group of the resulting compounds is split off as described above, and/or, if desired, the mercapto group is etherified in a manner known per se.

Those compounds of the general formula (I), wherein $R^2$ is a lower alkyl group having an etherified mercapto substituent, can also be prepared by reacting a reactive ester of a compound of the general formula (I), wherein $R^2$ is hydroxy-(lower)-alkyl, with a metal salt of the respective mercaptane.

The compounds of the general formula (I), wherein $R^2$ is a halo-(lower)-alkyl group, $R^6$ is a group of the general formula $R^7$—CO—, and $R^1$, $R^3$, $R^4$, $R^5$, $R^7$ and n are as defined above, can be reacted with an alkali metal nitrite, such as sodium or potassium nitrite, or with a noble metal nitrite, such as silver nitrite, in an appropriate solvent, such as diethyl ether, dimethylformamide, diethyleneglycol dimethyl ether, dimethylsulfoxide, sulfolane or hexamethylphosphoric triamide, at a temperature between about room temperature and 150° C., to obtain the respective compounds of the general formula (I), wherein $R^2$ is a nitro-(lower)-alkyl group. If desired, the $R^7$—CO— group of the resulting compounds can be split off as described above.

The compounds of the general formula (I), wherein $R^2$ is a halo-(lower)-alkyl group, $R^6$ stands for a group of the general formula $R^7$—CO—, and $R^1$, $R^3$, $R^4$, $R^5$, $R^7$ and n are as defined above, can also be related with an alkali cyanide, preferably sodium cyanide, to form the respective compounds of the general formula (I), wherein $R^2$ is cyano-(lower)-alkyl. The reaction is performed in an appropriate solvent, such as dimethylformamide, dimethylsulfoxide or hexamethylphosphoric triamide, at a temperature of about 80° C. to 150° C. The cyanide reactant is applied preferably in a 5 to 10-fold molar excess. If desired, the resulting cyano compound is stirred in an aqueous alkaline medium at room temperature to obtain the corresponding derivative wherein $R^6$ is hydrogen and $R^2$ is a carboxamido-(lower)-alkyl group. These latter compounds can be treated, if desired, with a mineral acid, such as hydrochloric acid or sulfuric acid, in an appropriate solvent, such as ethanol, isopropanol, butanol, water or mixtures thereof, at a temperature between room temperature and the boiling point of the reaction mixture, to obtain compounds of the general formula (I), wherein $R^2$ is a carboxy-(lower)-alkyl group and $R^6$ stands for hydrogen. If desired, these latter compounds can be converted into the respective esters by reacting them with an excess of a lower aliphatic mono- or diol at a temperature of about 0° C. to 100° C. in the presence of an anhydrous mineral acid, such as dry hydrochloric acid. The excess of the alcohol also serves as solvent for the starting substance.

Those compounds of the general formula (I), wherein $R^2$ is a lower alkyl group having a primary, secondary or tertiary amino substituent, can be prepared by reacting a compound of the general formula (I), wherein $R^2$ is a halo-(lower)-alkyl group, $R^6$ stands for a group of the general formula $R^7$—CO—, and $R^1$, $R^3$, $R^4$, $R^5$, $R^7$ and n are as defined above, with dry ammonia, a primary or secondary lower aliphatic amine or a cyclic amine containing 2 to 6 ring carbon atoms and optionally a further hetero atom, such as nitrogen, sulfur or oxygen atom. The reaction can be performed in the absence of a solvent or in a solvent medium, such as in acetone, acetonitrile, dimethylformamide, dimethylsulfoxide, hexamethylphosphoric triamide or sulfolane, at a temperature of about 0° C. to 150° C. If desired, the $R^7$—CO— group of the resulting compound can be split off as described above.

The compounds of the general formula (I), wherein $R^2$ represents a lower alkyl group having a primary amino substituent, can also be prepared by reducing a compound of the general formula (I), wherein $R^2$ is carboxamido-(lower)-alkyl, and $R^1$, $R^3$, $R^4$, $R^5$, $R^6$ and n are as defined above, with the hydride of a metal or a non-metallic element, a complex metal hydride, or—perferably—borane. The reaction can be performed e.g. in diethyl ether, tetrahydrofuran, dioxane, 1,2-dimethoxyethane or diethyleneglycol dimethyl ether.

Those compounds of the general formula (I), wherein $R^6$ is cyano, can be prepared by reacting a compound of the general formula (I), wherein $R^6$ is hydrogen and $R^1$, $R^2$, $R^3$, $R^4$, $R^5$ and n are as defined above, with a cyanogen halide, such as cyanogen bromide or cyanogen chloride. The reaction is performed in an appropriate solvent, such as benzene or its homologues, chloroform or 1,2-dichloroethane, at a temperature of about 0° C. to 50° C. If desired, the resulting cyano compounds can be treated with an aqueous mineral acid, such as hydrochloric acid or sulfuric acid, in a solvent, such as methanol, ethanol, n-propanol, isopropanol, water or mixtures thereof, at a temperature between room temperature and the boiling point of the reaction mixture, whereby compounds of the general formula (I), wherein $R^6$ is carboxamido group and $R^1$, $R^2$, $R^3$, $R^4$, $R^5$ and n are as defined above, are formed. These latter compounds can be reacted with an appropriate lower alkyl ester of chloroformic acid or pyrocarbonic acid in a solvent medium, such as chloroform or 1,2-dichloroethane, at a temperature between about room temperature and 50° C. to obtain compounds of the general formula (I), wherein $R^6$ is a carboxamido group having a lower alkoxycarbonyl substituent.

Those compounds of the general formula (I), wherein $R^6$ is a carboxamido group having a lower alkyl substituent, can be prepared by reacting a compound of the general formula (I), wherein $R^6$ is hydrogen and $R^1$, $R^2$, $R^3$, $R^4$, $R^5$ and n are as defined above, with a lower alkyl isocyanate in an appropriate solvent, such as a chlorinated hydrocarbon (e.g. chloroform or 1,2-dichloroethane), at a temperature between room temperature and the boiling point of the reaction mixture.

In order to liberate a base of the general formula (I) from its salt the salt is dissolved in water, methanol, ethanol, dimethylformamide or mixtures thereof, then an aqueous solution of sod or potassium hydroxide or a methanolic sodium methoxide solution is added, and the base is separated either by filtration or by extracting the mixture with an appropriate organic solvent, such as chloroform.

The acid addition salts of the compounds having the general formula (I) are prepared preferably so that the free base is dissolved in an appropriate solvent, such as methanol, ethanol, isopropanol or acetonitrile, then a solution of the acid in an appropriate solvent, preferably ethanol or isopropanol, is added, and the resulting salt is separated from the reaction mixture optionally after evaporating a part of the total amount of the solvent(s) present.

Some representatives of these acid addition salts can also be prepared by adding the free base to a hot (60° to 100° C.) aqueous and/or lower alcoholic solution of the respective acid, cooling the mixture, and separating the resulting crystalline salt.

In order to prepare the complexes of the compounds having the general formula (I) the free base of the general formula (I) and the inorganic salt are dissolved separately in an appropriate solvent, such as acetonitrile, ethyl acetate or a lower alkanol, admixing the solutions at a temperature between about room temperature and 100° C., and the crystalline complex salt separating upon cooling is filtered off.

Those compounds of the general formula (I), wherein one of $R^2$ and $R^3$ is hydrogen and the other is different from hydrogen, contain a centre of asymmetry (the carbon atom in position 4), thus they exist in the form of two optically active isomers. In order to separate the optically active isomers from each other the racemic compound is treated with 0.5 to 1.0 mole, calculated for 1 mole of the racemate, of an appropriate optically active acid, such as d-tartaric acid or O,O-dibenzoyl-d-tartaric acid in a solvent medium, such as methanol, ethanol or ethyl acetate. Depending on the acid applied, the separated salt is an essentially optically pure isomer or it is to be purified by repeated recrystallization steps to yield one of the isomers in pure state. The other isomer can be separated either as the free base or in the form of its salt by processing the mother liquors. The salts can be converted into the respective optically active bases by the method discussed above.

As mentioned above, the compounds of the invention possess valuable antiphlogistic and diuretic effects. Thus e.g. the $ED_{50}$ value of 1,3-bis(2',6'-dimethylphenyl)-2-imino-4-methyl-imidazolidine fumarate, determined on rats after oral administration in the carrageenin-induced plantar oedema test (see Lence et al.: Arch. Int. Pharmacodyn. 136, 237 /1962/; C. A. Winter: Proc. Soc. Exp. Biol. Med. 11, 544 /1962/), is 11 mg/kg, whereas Indomethacine, applied as reference substance, has an $ED_{50}$ value of 20 mg/kg in the same test. The above compound of the invention exhibits a considerable activity in the cotton granuloma test (C. A. Winter: J. Pharm. Exp. Ther. 141, 369 /1963/) and in the adjuvant arthritis test (B. B. Newbould: Brit. J. Pharmacol. Chemother. 21, 137 /1963/) as well.

1,3-Bis(2',6'-dimethylphenyl)-2-imino-4-methyl-imidazoline fumarate is far more advantageous than Indomethacine also with regard to its toxicological properties. The $LD_{50}$ value of this compound, determined on rats after oral administration, amounts to 150 mg/kg, whereas that of Indomethacine is only 20 mg/kg. Furthermore, the ulcerogeneous side effect of the new compound is far lower than that of Indomethacine, and the new compound decreases gastric acid secretion to a medium degree. Based on the above, the new compound according to the invention can be applied in the treatment of inflammatory disorders with a far greater degree of safety than Indomethacine. An interesting property of the above new compound is that its mode of action differs from that of the carboxylic acid type non-steroidal antiphlogistics; i.e. the new compound does not inhibit the function of prostaglandine synthetase enzyme, and its antiphlogistic effect is not connected with the blocking of serotonine or histamine receptors.

The following compounds of the invention also exert significant antiphthlogistic effects:

1,3-bis(2',6'-dimethylphenyl)-2-imino-4-chloromethyl-imidazolidine, 1,3-bis(2',6'-dimethylphenyl)-2-imino-imidazolidine-4-carboxylic acid, 1,3-bis(2',6'-dimethylphenyl)-2-imino-imidazolidine-4-acetamide, 1,3-bis(4'-chlorophenyl)-2-imino-4-methyl-imidazolidine, and 1-(4'-chlorophenyl)-2-imino-3-(2',6'-dimethylphenyl)-4-methylimidazolidine.

Some of the compounds according to the invention also exert favourable diuretic effects. Thus e.g., when examined by the Lipschitz test (Arch. int. Pharmacodyn. 137, 241 /1962/), 1-(1',3'-bis/2'',6''-dimethylphenyl/-4'-methyl-imidazolidin-2'-ylidene)-3-carbethoxy-thiourea increases the urine excretion of rats to the same degree as urea, applied as reference substance. The test results are given in Table 1.

TABLE 1

| Compound | Dosage mg/kg p.o. | No. of animals | Urine ml/kgx5 hr. |
|---|---|---|---|
| Control | — | 6 | 5.82 |
| Urea | 960 | 6 | 11.54 |
| 1-(1',3'-bis/2'',6''-dimethylphenyl/-4'-methyl-imidazolidin-2'-ylidene)-3-carbethoxy-thiourea | 25 | 6 | 11.16 |

Some of the new compounds according to the invention possess, beside their diuretic activity, a marked saluretic effect wth retention of potassium ions. This means that these compounds promote the excretion of sodium ions to a far greater extent than that of potassium ions, thus the sodium:potassium ratio measured in the urine is favourably high. The saluretic effect was examined on rats according to the method of Kagawa (J. Pharm. Exp. Ther. 126, 123 /1959/). The sodium:potassium ratio of the urine was decreased experimentally by introducing deoxycorticosterone acetate (DOCA) into the animals, and the DOCA-antagonizing effects of the compounds were measured. The effects of the two new compounds examined in this test were essentially the same as that of Spironolactone, utilized as reference substance. The test results are listed in Table 2.

TABLE 2

| Compound | Hormone substitution µg/animal s.c. | Dosage µg/animal p.o. | No. of animals | Effects* |
|---|---|---|---|---|
| DOCA | 12.5 | — | 4 | 0.75 |
| Spironolactone | 12.5 | 480 | 4 | 1.17 |
| 1-(1',3'-bis/2",6"-di-methyl phenyl/-4'-idazolidin-2'-yl-idene)-3-carbethoxy-thiourea | methyl-im- 12.5 | 480 | 8 | 1.02 |
| DOCA | 12.5 | — | 4 | 0.88 |
| Spironolactone | 12.5 | 480 | 4 | 1.19 |
| 1,3-bis(2',6'-dimethyl-phenyl)-2-carbethoxy-imino-4-methyl-imid-azolidine | 12.5 | 480 | 8 | 1.19 |

These results are particularly valuable because, as the compounds of the invention are non-steroidal derivatives, their potassium-retentive diuretic effect is not coupled with the undesired side-effects (primarily hormonal effects) of the steroids with related activities.

1,3-Bis(2',6'-dimethylphenyl)-2-(p-methoxy-benzyloxycarbonyl)-imino-4-methyl-imidazolidine shows a strong potassium-retentive diuretic effect as well.

Certain other representatives of the compounds according to the invention, such as 1,3-bis(2',6'-dimethylphenyl)-2-imino-4-methyl-imidazolidine, 1,3-bis(2',6'-dimethylphenyl)-2-imino-4,5-cis-dimethyl-imidazlidine, methyl 1,3-bis(2',6'-dimethylphenyl)-2-imino-imidazolidine-4-carboxylate acid and 1-(2',3'-dimethylphenyl)-2-imino-3-(4'-chlorophenyl)-4-methylimidazolidine, also exert potassium-retentive diuretic effect, they are, however, less effective than the compounds listed in Table 2.

Some of the compounds according to the invention, such as 1,3-bis(2',6'-dimethylphenyl)-2-imino-4-methyl-imidazolidine, also increase the spontaneous activity of isolated rat uterine horn (Gaddum: Brit. J. Pharm. 1954, 240) and of the longitudinal smooth muscle of guinea pig ileum (Paton and Vizi: J. Pharm. 1969, 10) when tested under in vitro conditions.

The compounds according to the invention can be applied in the therapy to treat inflammatory diseases and to provoke diuresis. For these purposes the compounds can be administered in the form of enterally, parenterally or locally applicable pharmaceutical compositions. Of the pharmaceutcal compositions the orally applicable ones (such as tablets, coated tablets and capsules) and the locally applicable ones (such as ointments) are the most preferred.

The pharmaceutical compositions may contain the compounds according to the invention either as the sole active ingredient or in combination with other substances of similar biological effects. The pharmaceutical compositions are prepared according to methods known per se, utilizing conventional pharmaceutical carriers, additives and/or auxiliary agents. Tablets for oral administration may contain, beside the active ingredient(s), e.g. carriers, such as glucose, lactose or mannitol, binding agents, such as gum arabic, gelatine, methyl cellulose, hydroxyethyl cellulose, pectin or polyvinyl pyrrolidine, disintegration aids, such as starch, ultraamylopectin, alginic acid or colloidal silica, furthermore glidants and lubricants, such as talc, magnesium stearate or polyoxyethylene.

The daily dosage of the compounds according to the invention varies generally between about 0.1 mg/kg and 20 mg/kg, preferably between about 1 mg/kg and 10 mg/kg. Of course, the actual dosage applied depends on other factors, such as the age, body weight and general condition of the patient to be treated, as well.

The invention is elucidated in detail by the aid of the following non-limiting Examples.

EXAMPLE 1

1,3-Bis(2',6'-dimethylphenyl)-2-imino-imidazolidine

Method (a)

500 ml of xylene are introduced into a 1 liter four-necked flask equipped with a stirrer, reflux condenser, thermometer and dropping funnel of 100 ml capacity. 72.5 g (0.27 moles) of 1,2-bis(2',6'-dimethylphenyl-amino)-ethane are dissolved in the xylene, and a solution of 33.9 g (0.32 moles) of cyanogen bromide in 200 ml of xylene is added dropwise, within about 1.5 hours, to the stirred solution at an internal temperature of 110° to 115° C. After the addition the mixture is stirred for a further hor at 110° to 115° C. and then it is allowed to cool. The separated precipitate is filtered off, washed with xylene and diethyl ether, and dried at room temperature. 100.5 g (99.4%) of 1,3-bis(2',6'-dimethylphenyl)-2-imino-imidazolidine hydrobromide are obtained as colourless crystals melting at 289°–290° C.

The free base is liberated from its salt as follows: The above salt is dissolved in about 1 liter of water, the solution is filtered, and the filtrate is rendered strongly alkaline by introducing 10 n aqueous sodium hydroxide solution. The separated colourless precipitate is filtered off, washed thoroughly with water, and dried at 40° to 50° C. 71.0 g (89.6%) of 1,3-bis(2',6'-dimethylphenyl)-2-imino-imidazolidine are obtained; m.p.: 188°–190° C.

1,2-Bis(2',6'-dimethylphenyl-amino)-ethane, utilized as starting substance, can be prepared e.g. as described by Shapiro et al. (loc. cit.).

Method (b)

One proceeds as described in Method (a) above with the only difference that chlorobenzene is applied as solvent instead of xylene. 1,3-Bis(2',6'-dimethylphenyl)-2-iminoimidazolidine hydrobromide is obtained with a yield of 85.7%.

Method (c)

300 ml of xylene are introduced into a 500 ml four-necked flask equipped with a stirrer, reflux condenser, thermometer and dropping funnel of 250 ml capacity. 31.8 g (0.3 moles) of cyanogen bromide are dissolved in the xylene, and a solution of 26.85 g (0.1 moles) of 1,2-bis(2',6'-dimethylphenylamino)-ethane in 150 ml of xylene is added dropwise, within about 1 hour, to the stirred solution at 50° to 55° C. The resulting mixture is stirred for an additional hour at 50° to 55° C. and then it is cooled. The separated precipitate is filtered off, washed with xylene and diethyl ether and dried at room temperature. The resulting 32.5 g of light beige 1,3-bis(2',6'-dimethylphenyl)-2-imino-imidazolidine hydrobromide are dissolved in about 700 ml of ethanol under boiling, the solution is decolourized with carbon, filtered, and about 700 ml of dry diethyl ether are added to the filtrate in order to precipitate the product. 30.5 g (81.5%) of the purified salt are obtained; m.p.: 292°–294° C.

Method (d)

0.5 g of yellow mercury(II)oxide are added to a solution of 0.5 g (1.53 mmoles) of 1-(2',6'-dimethylphenyl)-1-(β-/2',6'-dimethylphenyl-amino/-ethyl)-thiourea in 30 ml of xylene, and the mixture is boiled for 4 hours. The mixture is allowed to cool, the inorganic substances are separated by filtration, and the solvent is removed from the filtrate under reduced pressure. The residual thick, yellow oil, weighing 0.5 g, is dissolved in 5 ml of 1 n aqueous hydrochloric acid, the insolubles are filtered off, and the filtrate is rendered alkaline with 2 n aqueous sodium hydroxide solution. The separated precipitate is filtered off, washed with water, and dried. 0.32 g (71.3%) of 1,3-bis(2',6'-dimethylphenyl)-2-imino-imidazolidine are obtained; m.p.: 187°–189° C.

1-(2',6'-dimethylphenyl)-1-(β-/2',6'-dimethyl-phenylamino/-ethyl)-thiourea, applied as starting substance in the above process, can be prepared as follows:

(a) A solution of 5.35 g (20 mmoles) of 1,2-bis(2',6'-dimethylphenyl-amino)-ethane in 30 ml of dry chloroform is added dropwise, within about 20 minutes, to a solution of 3.6 g (22 mmoles) of benzoyl isothiocyanate (D.T. Elmore and J. R. Ogle, loc. cit.) in 40 ml of dry acetone at room temperature. The resulting mixture is stirred for 6 hours at room temperature, and next day it is boiled for 2 hours. The solvents are distilled off, and the resulting semisolid substance, weighing 10.7 g, is triturated with 30 ml of isopropanol at 50° C. 7.2 g (83.4%) of colourless, crystalline 1-benzoyl-3-(2',6'-dimethylphenyl)-3-(β-/2',6'-dimethylphenyl-amino/-ethyl)-thiourea are obtained; m.p.: 135°–136° C.

(b) 2.16 g (5 mmoles) of 1-benzoyl-3-(2',6'-dimethyl-phenyl)-3-(β-/2',6'-dimethylphenyl-amino/-ethyl)-thiourea, prepared as described in point (a) above, are added to a solution of 3.0 g (53.6 mmoles) of potassium hydroxide in 30 ml of water and 50 ml of ethanol, and the resulting mixture is boiled for 3 hours. The mixture is cooled and poured onto 300 ml of icy water. The separated crystalline substance is filtered off, washed with water, and dried at 40° to 50° C. 1.31 g (80.3%) of crude 1-(2',6'-dimethylphenyl)-1-(β-/2',6'-dimethylphenyl-amino/-ethyl)-thiourea, melting at 146°–148° C., are obtained. The product melts at 149°–150° C. after recrystallization from cyclohexane.

EXAMPLE 2

1,3-Bis(2',6'-dimethylphenyl)-2-imino-hexahydropyrimidine

A solution of 0.75 g (7.1 mmoles) of cyanogen bromide in 10 ml of n-butanol is added dropwise, within about 0.5 hours, to a stirred solution of 2.0 g (7.1 mmole) of 1,3-bis(2',6'-dimethylphenyl-amino)-propane in 20 ml of n-butanol at 110° to 115° C. After the addition the mixture is stirred for further 2 hours at the same temperature. Thereafter the mixture is cooled, shaken five times with 10 ml of water each, the aqueous solutions are combined, and the pH of the mixture is adjusted to 8.0 to 8.5 with concentrated aqueous ammonia. The separated unreacted starting substance (0.4 g, m.p.: 68°–71° C.) is filtered off, the aqueous filtrate is rendered alkaline with 2 n aqueous sodium hydroxide solution, and the aqueous-alkaline phase is extracted thrice with 30 ml of chloroform each. The organic phases are combined, washed with water, dried over potassium carbonate, and the solvent is distilled off. 0.8 g (36.7%) of 1,3-bis(2',6'-dimethylphenyl)-2-imino-hexahydropyrimidine are obtained; m.p.: 181°–183° C. (after recrystallization from aqueous isopropenol).

1,3-Bis(2',6'-dimethylphenyl-amino)-propane, applied as starting substance in the above process, can be prepared e.g. by the method of Shapiro et al. (loc. cit.).

The compounds listed in Examples 3 to 31 are prepared as described in Method (a) of Example 1, utilizing appropriately substituted ethylenediamine or propylenediamine derivatives as starting substances.

EXAMPLE 3

1,3-Bis(2',6'-dimethylphenyl)-2-imino-4-methylimidazolidine

M.p.: 124°–125° C.; yield: 84.4%.

1,2-Bis(2',6'-dimethylphenyl-amino)-propane, utilized as starting substance, is prepared as follows:

Method (a)

2,6-Dimethylaniline is reacted with 1,2-dibromopropane as described by Shapiro et al. (loc. cit.) to obtained the aimed compound with a yield of 18.6%.

Method (b)

(a) A solution of 123 ml (202 g, 1.7 moles) of thionyl chloride in 200 ml of dry benzene is added dropwise to a solution of 100 g (0.558 moles) of N-(β-hydroxypropyl)-2,6-dimethyl-aniline (prepared from 2,6-dimethylaniline and 1,2-epoxipropane as described in the published Dutch patent application No. 6,507,312; b.p.: 120°–125° C./1 mm Hg; yield: 51%) in 1000 ml of dry benzene at room temperature under nitrogen atmosphere. The resulting mixture is stirred and boiled under nitrogen atmosphere for 5 hours. The mixture is cooled with icy water, 100 ml of water are added dropwise to the cooled mixture, and the pH of the resulting mixture is adjusted to 9 with 10 n aqueous sodium hydroxide solution. The phases are separated from each other, and the aqueous phase is extracted thrice with 200 ml of benzene each. The organic solutions are combined, washed thrice with 300 ml of water each, dried over anhydrous sodium sulfate, and the solvent is evaporated under reduced pressure. The residual dark brown oil is divided into two parts of about equal weights, and then distilled under reduced pressure. 85 g (77%) of N-(β- chloropropyl)-2,6-dimethyl-aniline are obtained as a colourless oil boiling at 105°–108° C./0.8 mm Hg.

(b) A mixture of 86 g (0.435 moles) of N-(β-chloropropyl)-2,6-dimethyl-aniline, prepared as described in point (a) above, 110 ml (107.4 g, 0.88 moles) of 2,6-dimethylaniline and 4.2 g (25 mmoles) of potassium iodide is stirred at 140° to 145° C. for 3 hours under nitrogen atmosphere. The mixture is allowed to cool to about 80° C., 300 ml of isopropanol are added, the resulting mixture is allowed to cool to room temperature under stirring, and then allowed to stand overnight. The separated precipitate is filtered off, washed with cold (+5° C.) isopropanol and dried. 67.1 g (42.4%) of crude 1,2-bis(2',6'-dimethylphenyl-amino)-propane hydrochloride (fraction A) are obtained. The filtrate is admixed with 200 ml of 20% aqueous hydrochloric acid, and the mixture is allowed to stand for 24 hours. The separated precipitate is filtered off, washed with water and dried. In this way further 48 g (34.6%) of crude 1,2-bis(2',6'-dimethylphenyl-amino)-propane hydrochloride (fraction B) are obtained, thus the total yield is 83.0%. Fractions A and B are combined, dissolved in a mixture of 500 ml of dimethyl formamide and 250 ml of water, and the solution is rendered alkaline (pH=10) with 10 n aqueous sodium hydroxide solution. The solution is admixed with 2 liters of water, the separated precipitate is filtered off, washed with water, and dried. 87.15 g (70.9%) of 1,2-bis(2',6'-dimethylphenyl-amino)-propane (m.p.: 52°–55° C.) are obtained. This product is sufficiently pure to apply it directly in the next step.

Method (c)

(a) A mixture of 250 ml (712 g, 2.63 moles) of phosphorous tribromide and 250 ml of dry chloroform is added dropwise to a solution of 100 g (0.558 moles) of N-(β-hydroxypropyl)-2,6-dimethyl-aniline in 500 ml of dry chloroform. During the addition the temperature of the mixture is maintained below +25° C. by cooling with icy water. The resulting mixture is boiled for 6 hours, thereafter it is cooled on salted ice, and 100 ml of water are added dropwise. The pH of the resulting mixture is adjusted to 9 with 10 n aqueous sodium hydroxide solutions. The phases are separated from each other, and the aqueous phase is extracted thrice with 300 ml of chloroform each. The organic solutions are combined, washed four times with 500 ml of water each, dried over anhydrous sodium sulfate, and the solvent is evaporated under reduced pressure. 118.2 g (87.5%) of N-(β-bromopropyl)-2,6-dimethyl-aniline are obtained as a colourless oily residue. This product is sufficiently pure to be applied directly in the next step. When distilling the oil at 0.3 mm Hg it boils at 102°–106° C.

(b) A mixture of 106.8 g (0.441 moles) of N-(β-bromopropyl)-2,6-dimethyl-aniline, obtained as described in point (a) above, 110 ml (107.4 g, 0.88 moles) of 2,6-dimethyl-aniline and 1.6 g (10 mmoles) of potassium iodide is stirred at 100° to 105° C. for 3 hours under nitrogen atmosphere. The mixture is allowed to cool, 600 ml of 10% aqueous hydrochloric acid are added, and the resulting mixture is allowed to stand at room temperature overnight. The separated precipitate, which is a mixture of the hydrochloride and the hydrobromide of the expected product, is filtered off, washed with water, dried, and then treated as described in point (b) of Method (b) above in order to liberate the base. In this way 93.8 g (75.3%) of 1,2-bis(2',6'-dimethylphenyl-amino)-propane are obtained; m.p.: 54°–56° C.

Method (d)

A solution of 4.8 ml (7.1 g, 0.062 moles) of methanesulfonyl chloride in 10 ml of 1,2-dichloroethane is added dropwise, at 5° to 10° C., to a stirred solution of 10.0 g (0.0556 moles) of N-(β-hydroxypropyl)-2,6-dimethyl-aniline and 8.5 ml (6.2 g, 0.0612 moles) of triethylamine in 50 ml of 1,2-dichloroethane. The mixture is stirred for additional 30 minutes at 5° to 10° C., thereafter the separated triethylamine salt is filtered off, washed with 1,2-dichloroethane, and the filtrate is added dropwise, under nitrogen atmosphere, to a stirred solution of 13.9 ml (13.6 g, 0.112 moles) of 2,6-dimethylaniline in 20 ml of 1,2-dichloroethane at 80° to 85° C. The resulting mixture is stirred and boiled for a further hour, thereafter it is cooled, the separated salt of 2,6-dimethylaniline is filtered off, and the filtrate is evaporated under reduced pressure. 150 ml of 1 n aqueous hydrochloric acid are added to the thick, oily residue, and the mixture is stirred for one hour. The separated crude solid, which is the hydrochloride of the expected product, is filtered off, washed with water, and dried. 13.5 g of the crude hydrochloride are obtained. This salt is treated as described in point (b) of Method (b) above in order to liberate the base. 9.4 g (60%) of 1,2-bis(2',6'-dimethylphenyl-amino)-propane are obtained; m.p.: 53°–55° C.

EXAMPLE 4

1,3-Bis(2',6'-dimethylphenyl)-2-imino-4-n-butylimidazolidine

EXAMPLE 5

1,3-Bis(2',6'-dimethylphenyl)-2-imino-4-trifluoromethyl-imidazolidine

EXAMPLE 6

1,3-Bis(2',6'-dimethylphenyl)-2-imino-4-hydroxymethyl-imidazolidine

M.p.: 244°–245° C.; yield: 96.8%.

2,3-Bis(2',6'-dimethylphenyl-amino)-1-propanol, applied as starting substance, is prepared as follows:

A mixture of 109 g (0.5 moles) of 2,3-dibromo-propan-1-ol, 248 ml (242.4 g, 2.0 moles) of 2,6-dimethylaniline and 1.0 g (6 mmoles) of potassium iodide is stirred at 140° to 145° C. for 3 hours under nitrogen atmosphere. The mixture is allowed to cool to about 80° C., and 100 ml of isopropanol, followed by 500 ml of 20% aqueous hydrochloric acid, are added. The mixture is allowed to stand overnight, thereafter the separated precipitate is filtered off, washed with water and dried. The resulting solid, weighing 170 g, is dissolved in 1500 ml of methanol, the pH of the solution is adjusted to 10 with 10 n aqueous sodium hydroxide solution, and the mixture is diluted with 1500 ml of water. The separated precipitate is filtered off, washed with water and dried. 99 g (66.4%) of crude 2,3-bis(2',6'-dimethylphenyl-amino)-1-propanol are obtained. The product melts at 92°–94° C. after recrystallization from methanol.

EXAMPLE 7

1,3-Bis(2',6'-dimethylphenyl)-2-imino-hexahydropyrimidine

M.p.: 184°–186° C.; yield: 39.6%.

The product is identical with that obtained according to Example 2.

EXAMPLE 8

1,3-Bis(2',6'-dimethylphenyl)-2-imino-4-methylhexahydro-pyrimidine

M.p.: 194°–196° C.; yield: 88.6%.

1,3-Bis(2',6'-dimethylphenyl-amino)-butane, applied as starting substance, can be prepared e.g. by the method of Shapiro et al. (loc. cit.), utilizing 2,6-dimethylaniline and 1,3-dibromobutane as starting materials. The free base boils at 159°–160° C./0.1 mm Hg, and the hydrochloride melts at 178°–180° C. Yield: 45.6%.

EXAMPLE 9

1,3-Bis(2',6'-dimethylphenyl)-2-imino-4,4-dimethylimidazolidine

M.p.: 171°–174° C.; yield: 38.9%.

1,2-Bis(2',6'-dimethylphenyl-amino)-2-methyl-propane, applied as starting substance, is prepared as follows:

(a) A mixture of 7.0 g (0.037 moles) of N-methacryloyl-2,6-dimethyl-aniline (prepared e.g. by acylating 2,6-dimethylaniline with methacryloyl chloride in diethyl ether; m.p.: 110°–112° C.) and 9.3 ml (9.1 g, 0.075 moles) of 2,6-dimethylaniline is maintained at 220° C. for 2 hours under nitrogen atmosphere. The mixture is allowed to cool and then triturated with 80 ml of 1 n aqueous hydrochloric acid. The separated crystalline crude product is filtered off, washed with water and dried. The crude product is dissolved in 200 ml of hot isopropanol, the insolubles are filtered off, and the filtrate is allowed to cool. The separated crystalline substance is filtered off, washed with isopropanol and dried. 4.0 g of N-(β-/2,6-dimethylphenyl-amino/-isobutyryl)-2,6-dimethyl-aniline are obtained. The filtrate is concentrated to a volume of about 20 ml. Further 1.1 g of the above substance separate from the concentrate, thus a total amount of 5.1 g (44.3%) of N-(α-/2,6-dimethylphenyl-amino/-isobutyryl)-2,6-dimethyl-aniline are obtained; m.p.: 141°–143° C.

(b) A solution of 4.0 g (0.0129 moles) of N-(α-/2,6-dimethylphenyl-amino/-isobutyryl)-2,6-dimethyl-aniline, prepared as described in point (a) above, in 40 ml of dry tetrahydrofuran is added dropwise at 5° to 10° C. to 24 ml of a stirred 1.68 molar borane solution in tetrahydrofuran. The resulting mixture is stirred and boiled for 4 hours. Thereafter the mixture is cooled, 8 ml of the above borane solution are added, and boiling is continued for additional 4 hours. The mixture is cooled on an ice bath, 25 ml of 20% aqueous hydrochloric acid are added dropwise, and tetrahydrofuran is evaporated under reduced pressure. The residual aqueous mixture is diluted with 200 ml of water, rendered alkaline with 5 n aqueous sodium hydroxide solution, and then extracted thrice with 70 ml of diethyl ether each. The etheral solutions are combined, washed thrice with 20 ml of water each, dried over anhydrous magnesium sulfate, and the solvent is evaporated under reduced pressure. The oily residue is triturated with diisopropyl ether to obtain 1.8 g of the unreacted starting amide as a crystalline substance. This substance is filtered off and the filtrate is evaporated under reduced pressure. The crude 1,2-bis(2',6'-dimethylphenyl-amino)-2-methyl-propane is obtained with a quantitative yield calculated for the amide converted. The product is purified through its hydrochloride (m.p.: 150°–152° C.). The pure base melts at 30°–31° C.

EXAMPLE 10

1,3-Bis(2',6'-dimethylphenyl)-2-imino-4,5-cis-dimethylimidazolidine

M.p.: 220°–221° C. (fumarate); yield: 49.1%.

Meso-2,3-bis(2',6'-dimethylphenyl-amino)-butane, applied as starting substance to prepared the above compound, furthermore racemic 2,3-bis(2',6'-dimethylphenyl-amino)-butane, applied as starting substance to prepare the compound of Example 11, are produced as follows:

(a) A mixture of 37.2 ml (36.3 g, 0.3 moles) of 2,6-dimethylaniline, 13.1 ml (12.9 g, 0.15 moles) of 2,3-butanedione and 100 ml of ethanol is boiled for 12 hours. The solvent is evaporated under reduced pressure, 80 ml of water and 20 ml of acetic acid are added to the residue, and the resulting mixture is stirred for 6 hours at 0° to ±5° C. The mixture is allowed to stand overnight, thereafter the separated precipitate is filtered off, washed with water and dried. 34.0 g (77.5%) of crude 2,3-bis(2',6'-dimethylphenyl-imino)-butane are obtained; m.p.: 78°–86° C. After recrystallization from ethanol 25.1 g (57.2%) of the pure substance, melting at 88°–90° C., are obtained.

(b) 11.6 g (0.308 moles) of solid sodium borohydride are added in small portions, within about 0.5 hours, to a vigorously stirred suspension of 30 g (0.103 moles) of 2,3-bis(2',6'-dimethylphenyl-imino)-butane in 600 ml of methanol at room temperature. The resulting mixture is stirred and boiled for one hour, then it is cooled to room temperature, further 11.6 g of solid sodium borohydride are added as described above, and boiling is continued for an additional hour. The solvent is evaporated under reduced pressure, the residue is admixed with 200 ml of water, and the resulting mixture is extracted thrice with 200 ml of benzene each. The benzene solutions are combined, dried over anhydrous potassium carbonate, and the solvent is evaporated under reduced pressure. The residue, weighing 31.3 g, is dissolved in 500 ml of isopropanol, 100 ml of isopropanolic hydrochloric acid (containing about 15 g of acid/100 ml) are aded, and the mixture is allowed to stand at 0° C. for 2 hours. The separated precipitate is filtered off, washed with cold isopropanol and dried. 26.4 g of the hydrochloride of the expected product are obtained.

The hydrochloride obtained as described above is dissolved in 300 ml of dimethylformamide, the solution is rendered alkaline with concentrated aqueous ammonia, diluted with 1 liter of water, and the mixture is extracted thrice with 200 ml of diethyl ether each. The organic solutions are combined, washed thrice with 100 ml of water each, dried over anhydrous potassium carbonate, filtered, and the solvent is evaporated. 18.8 g (61.8%) of the product, consisting of a mixture of meso and racemic 2,3-bis(2',6'-dimethylphenyl-amino)-butane, are obtained.

This isomeric mixture is subjected to chromatography on a column filled with 500 g of silica gel, applying a 8:1 mixture of benzene and ethyl acetate as eluting agent. The following substances are obtained: 10 g (32.9%) of meso-2,3-bis(2',6'-dimethylphenyl-amino)-butane; $R_f=0.9$, m.p.: 100°–101° C. (after recrystallization from hexane), and 6.4 g (21.1%) of racemic 2,3-bis(2',6'-dimethylphenyl-amino)-butane; $R_f=0.75$, m.p.: 41°–43° C. (after recrystallization from petroleum ether).

EXAMPLE 11

1,3-Bis(2',6'-dimethylphenyl)-2-imino-4,5-transdimethyl-imidazolidine

M.p.: 155°–157° C. (furmarate); yield: 58.2%.

Racemic 2,3-bis(2',6'-dimethylphenyl-amino)-butane, applied as starting substance, is prepared as described in Example 10.

EXAMPLE 12

1,3-Bis(2',3'-dimethylphenyl)-2-imino-imidazolidine
M.p.: 123°–125° C.; yield: 54.2%.

1,2-Bis(2',3'-dimethylphenyl-amino)-ethane, applied as starting substance, is prepared by the method of Shapiro et al. (loc. cit.), modified as indicated below:

246 ml (242.4 g, 2.0 moles) of 2,3-dimethylaniline are added dropwise, within 1.5 hours, to a stirred and boiled solution of 43 ml (94 g, 0.5 moles) of 1,2-dibromoethane in 500 ml of xylene. After the addition the mixture is stirred for one hour at 140° C. and then allowed to stand. Next day the separated precipitate is filtered off, washed with benzene and dried. 259.3 g of the hydrobromide of the expected compound (fraction A) are obtained. The filtrate is evaporated in vacuo, the residue is triturated with isopropanol, the separated precipitate is filtered off, washed with cold isopropanol and dried. Additional 30 g of the above compound (fraction B) are obtained. Fractions A and B are combined, dissolved in 1000 ml of dimethylformamide, the solution is rendered alkaline with a 10 n aqueous sodium hydroxide solution under stirring and cooling with ice, and then diluted with 2 liters of water. The separated precipitate is filtered off, washed with water and dried. 84.3 g (62.8%) of 1,2-bis(2',3'-dimethylphenyl-amino)-ethane are obtained; m.p.: 130°–133° C.

EXAMPLE 13

1,3-Bis(2',3'-dimethylphenyl)-2-imino-4-methyl-imidazolidine

M.p.: 162°–164° C.; yield: 59.2%. The given melting point relates to the difumarate.

1,2-Bis(2',3'-dimethylphenyl-amino)-propane, applied as starting substance, is prepared as follows:

(a) 2,3-Dimethylaniline is reacted with 1,2-epoxypropane as described in Example 3, Method (b), point (a) to obtain N-(β-hydroxypropyl)-2,3-dimethylaniline; b.p.: 153°–155° C./1 mm Hg, yield: 71.8%.

(b) N-(β-Hydroxypropyl)-2,3-dimethyl-aniline, prepared as indicated in point (a) above, is converted into N-(β-bromopropyl)-2,3-dimethyl-aniline as described in Example 3, Method (c), point (a). The product, boiling at 134°–136° C./1 mm Hg, is obtained with a yield of 65.1%.

(c) N-(β-Bromopropyl)-2,3-dimethyl-aniline, prepared as indicated in point (b) above, is reacted with 2,3-dimethyl-aniline as given in Example 3, Method (c), point (b) to obtain 1,2-bis(2',3'-dimethylphenyl-amino)-propane with a yield of 84.2%. The hydrobromide of the product melts at 204°–208° C.

EXAMPLE 14

1-(2',6'-Dimethylphenyl)-2-imino-3-(2',3'-dimethylphenyl)-4-methyl-imidazolidine M.p.: 186°–188° C. (difumarate); yield: 95.4%.

1-(2',6'-dimethylphenyl-amino)-2-(2',3'-dimethylphenyl-amino)-propane, applied as starting substance, is prepared as follows:

A mixture of 29.5 g (0.15 moles) of N-(β-chloropropyl)-2,6-dimethyl-aniline, prepared as described in Example 3, Method (b), point (a), 37.2 ml (36.3 g, 0.3 moles) of 2,3-dimethylaniline and 0.5 g (3 mmoles) of potassium iodide is stirred at 100° to 105° C. for 3 hours under nitrogen atmosphere. The mixture is allowed to cool, admixed with 30 ml of isopropanol, the separated precipitate is filtered off, washed with cold isopropanol and dried. In this way 14.25 g (30.2%) of 2,3-dimethylaniline hydrochloride are separated. The filtrate is admixed with 200 ml of water, the mixture is acidified with 20% aqueous hydrochloric acid, the separated precipitate is filtered off, washed with water and dried. 30.2 g (56.7%) of 1-(2',6'-dimethylphenyl-amino)-2-(2',3'-dimethylphenyl-amino)-propane dihydrochloride are obtained. This salt is treated as described in Example 3, Method (b) point (c) to obtain the free base. The base is isolated by extracting the mixture with chloroform. The resulting substance is an oil at room temperature.

EXAMPLE 15

1-(2',3'-Dimethylphenyl)-2-imino-3-(2',6'-dimethylphenyl)-4-methyl-imidazolidine M.p.: 165°–167° C. (difumarate); yield: 54.6%.

1-(2',3'-Dimethylphenyl-amino)-2-(2',6'-dimethylphenyl-amino)-propane, applied as starting substance, is prepared as follows.

N-(β-Bromopropyl)-2,3-dimethyl-aniline, prepared as described in Example 13, point (b), is reacted with 2,6-dimethylaniline as described in Example 3, Method (c), point (b) to obtain the desired substance with a yield of 29.0%. The hydrochloride of the base melts at 182°–184° C.

EXAMPLE 16

1,3-Bis(2',4',6'-trimethylphenyl)-2-imino-4-methyl-imidazolidine

M.p.: 188°–189° C.; yield: 71.0%.

1,2-Bis(2',4',6'-trimethylphenyl-amino)-propane, applied as starting substance, is prepared as follows:

(a) 2,4,6-Trimethylaniline is reacted with 1,2-epoxypropane as described in Example 3, Method (b), point (a) to obtain N-(β-hydroxy-propyl)-2,4,6-trimethyl-aniline with a yield of 45.1%; b.p.: 130°–135° C./0.4 mm Hg.

(b) N-(β-Hydroxypropyl)-2,4,6-trimethyl-aniline, prepared as indicated in point (a) above, is treated as described in Example 3, Method (b), point (a) to obtain N-(β-chloropropyl)-2,4,6-trimethyl-aniline with a yield of 87.6%; b.p.: 110°–118° C./0.3 mm Hg.

(c) 32.75 g (0.155 moles) of N-(β-chloropropyl)-2,4,6-trimethyl-aniline, prepared as indicated in point (b) above, are reacted with 41.8 g (0.31 moles) of 2,4,6-trimethyl-aniline in the presence of 1.0 g (6 mmoles) of potassium iodide as described in Example 3, Method (b), point (b). The resulting mixture is admixed with 50 ml of diethyl ether, the separated precipitate is filtered off, washed with diethyl ether and dried. 24.8 g (46.6%) of 2,4,6-trimethylaniline hydrochloride are obtained. The filtrate is acidified with isopropanolic hydrochloric acid (acid content: about 15 g/100 ml), and the resulting mixture is maintained at 0° to +5° for 2 hours. The separated precipitate is filtered off, washed with cold isopropanol, and dried. 50.3 g (84.8%) of 1,2-bis(2',4',6'-trimethylphenyl-amino)-propane dihydrochloride are obtained; m.p.: 172°–173° C. The base is liberated from this salt as described in Example 3, Method (b), point (b), and is separated from the reaction mixture by chloroform extraction.

EXAMPLE 17

1-(2',6'-Dimethylphenyl)-2-imino-3-(2',4',6'-trimethylphenyl)-4-methyl-imidazolidine M.p.: 147.5°–150° C.; yield: 63.7%.

1-(2',6'-Dimethylphenyl-amino)-2-(2',4',6'-trimethylphenyl-amino)-propane, applied as starting substance, is prepared by reacting N-($\beta$-chloropropyl)-2,6-dimethyl-aniline, a compound prepared according to Example 3, Method (b), point (a), with 2,4,6-trimethylaniline under the conditions specified in Example 16, point (c). The aimed compound is obtained with a yield of 87.6%; m.p.: 128°–130° C. (dihydrochloride).

EXAMPLE 18

1-(2',4',6'-Trimethylphenyl)-2-imino-3-(2',6'-dimethylphenyl)-4-methyl-imidazolidine M.p.: 191°–193° C.; yield: 83.9%.

1-(2',4',6'-Trimethylphenyl-amino)-2-(2',6'-dimethylphenyl-amino)-propane, applied as starting substance, is obtained with a yield of 65.6% by reacting N-($\beta$-chloropropyl)-2,4,6-trimethyl-aniline, a compound prepared according to Example 16, point (b), with 2,6-dimethylaniline under the conditions given in Example 16, point (c). The hydrochloride of the product melts at 174°–177° C.

EXAMPLE 19

1,3-Bis(2',6'-diethylphenyl)-4-methyl-imidazolidine

M.p.: 143°–145° C. (hydrochloride); yield: 44.8%.

1,2-Bis(2',6'-diethylphenylamino)-propane, applied as starting substance, is prepared as follows:

(a) 2,6-Diethylaniline is reacted with 1,2-epoxypropane as described in Example 3, Method (b), point (a) to obtain N-($\beta$-hydroxypropyl)-2,6-diethylaniline with a yield of 44.7%; b.p.: 137°–145° C./1 mm Hg.

(b) N-($\beta$-Hydroxypropyl)-2,6-diethyl-aniline, obtained as indicated in point (a) above, is treated as described in Example 3, Method (b), point (a) to obtain N-($\beta$-chloropropyl)-2,6-diethyl-aniline with a yield of 69.1%; b.p.: 114°–120° C./1 mm Hg.

(c) A mixture of 46.3 g (0.205 moles) of N-($\beta$-chloropropyl)-2,6-diethyl-aniline, obtained as indicated in point (b) above, 61.2 g (0.41 moles) of 2,6-diethylaniline and 1.66 g (10 mmoles) of potassium iodide is stirred at 140° to 145° C. for 4 hours under nitrogen atmosphere. The mixture is allowed to cool, 150 ml of isopropanol are added, and the resulting mixture is stirred at 0° to +5° C. for 2 hours. The separated 2,6-diethylaniline hydrochloride (19.2 g, 25.2%) is filtered off, washed with cold isopropanol and dried. The filtrate is acidified with isopropanolic hydrochloric acid (acid content: about 15 g/100 ml), the separated precipitate is filtered off, washed with cold isopropanol and dried. The resulting crude substance, weighing 72 g, is recrystallized from methanol to obtain 29.4 g (34.8%) of 1,2-bis(2',6'-diethylphenyl-amino)-propane dihydrochloride as a uniform substance; m.p.: 161°–167° C. The base is liberated from this salt as described in point (c) of Example 16 and isolated from the reaction mixture by extraction with chloroform.

EXAMPLE 20

1,3-Bis(4'-methoxyphenyl)-2-imino-imidazolidine

M.p.: 194°–195° C.; yield: 91.0%.

1,2-Bis(4'-methoxyphenyl-amino)-propane, applied as starting substance, can be prepared e.g. by the method of McKay and Tarlton (loc. cit.) with a yield of 91.0% (yield reported in the literature: 97.9%).

EXAMPLE 21

1,3-Bis(4'-methoxyphenyl)-2-imino-4-methyl-imidazolidine

M.p.: 154°–156° C.; yield: 85.5%.

1,2-Bis(4'-methoxyphenyl-amino)-propane, applied as starting substance, is obtained with a yield of 32.7% by reacting 4-methoxyaniline with 1,2-dibromopropane as described by McKay and Tarlton (loc. cit.). The compound melts at 82°–84° C.

EXAMPLE 22

1-(2',6'-Dimethylphenyl)-2-imino-3-(4'-methoxyphenyl)-4-methyl-imidazolidine

M.p.: 150°–152° C. (difumarate); yield: 61.2%.

1-(2',6'-Dimethylphenyl-amino)-2-(4'-methoxyphenylamino)-propane, applied as starting substance, is prepared by reacting N-($\beta$-chloropropyl)-2,6-dimethyl-aniline, a compound obtained as described in Example 3, Method (b), point (a), with 4-methoxyaniline. The reaction is performed as described in Example 16, point (c), with the difference that the temperature is 100° to 105° C., and crystalline 4-methoxyaniline hydrochloride is removed from the mixture by triturating it with ethyl acetate. The product, melting at 160°–170° C. (dihydrochloride), is obtained with a yield of 64.0%.

EXAMPLE 23

1,3-Bis(3'-trifluoromethylphenyl)-2-imino-4-methyl-imidazolidine

M.p.: 67°–69° C.; yield: 44.4%.

1,2-Bis(3'-trifluoromethylphenyl-amino)-propane, applied as starting substance, is prepared as follows:

(a) 3-Trifluoromethylaniline is reacted with 1,2-epoxy-propane as described in Example 3, Method (b), point (a) to obtain N-($\beta$-hydroxypropyl)-3-trifluoromethyl-aniline with a yield of 61.5%; b.p.: 112°–118° C./0.5 mm Hg.

(b) N-($\beta$-Hydroxypropyl)-3-trifluoromethyl-aniline, prepared as indicated in point (a) above, is treated as described in Example 3, Method (b), point (a) to obtain N-($\beta$-chloropropyl)-3-trifluoromethyl-aniline with a yield of 81.0%; b.p.: 102°–103° C./0.4 mm Hg.

(c) N-($\beta$-Chloropropyl)-3-trifluoromethyl-aniline is reacted with 3-trifluoromethylaniline as described in Example 16, point (c) to obtain 1,2-bis(3'-trifluoromethylphenyl-amino)-propane with a yield of 76.6%. The dihydrochloride of this base melts at 116°–120° C.

EXAMPLE 24

1-(2',6'-Dimethylphenyl)-2-imino-3-(3'-trifluoromethylphenyl)-4-methyl-imidazolidine M.p.: 86°–90° C. (fumarate); yield: 80.6%.

1-(2',6'-Dimethylphenyl-amino)-2-(3'-trifluoromethylphenyl-amino)-propane, applied as starting substance, is prepared by reacting N-($\beta$-chloropropyl)-2,6- dimethyl-aniline, a compound prepared as described in Example 3, Method (b), point (a), with 3-trifluoromethyl-aniline. The reaction is performed as described in Example 16, point (c) with the difference that crystalline 3-trifluoromethyl-aniline hydrochloride is separated from the reaction mixture by trituration with benzene. The aimed product is obtained with a yield of 42.4%; m.p.: 160°–166° C. (dihydrochloride).

EXAMPLE 25

1-(3'-Trifluoromethylphenyl)-2-imino-3-(2',6'-dimethylphenyl)-4-methyl-imidazolidine M.p.: 146°–149° C. (fumarate); yield: 28.4%.

1-(3'-Trifluoromethylphenyl)-amino)-2-(2',6'-dimethylphenyl-amino)-propane, applied as starting substance, is prepared by reacting N-(β-chloropropyl)-3-trifluoromethylaniline, a compound obtained as described in Example 23, point (b), with 2,6-dimethylaniline. The reaction is performed as described in Example 16, point (c) with the difference that crystalline 2,6-dimethylaniline hydrochloride is separated from the reaction mixture by trituration with ethyl acetate. The aimed product is obtained with a yield of 55.6%; m.p.: 95°–98° C. (dihydrochloride).

EXAMPLE 26

1-(2'-Chloro-6'-methyl-phenyl)-2-imino-3-(2',6'-dimethylphenyl)-4-methyl-imidazolidine M.p.: 173°–175° C. (fumarate); yield: 40.5%.

1-(2'-Chloro-6'-methyl-phenyl-amino)-2-(2',6'-dimethylphenyl-amino)-propane, applied as starting substance, is prepared as follows:

(a) 2-Chloro-6-methyl-aniline is reacted with 1,2-epoxypropane as described in Example 3, Method (b), point (a) to obtain N-(β-hydroxypropyl)-2-chloro-6-methyl-aniline with a yield of 30.1%; b.p.: 118°–122° C./0.2 mm Hg.

(b) N-(β-Hydroxypropyl)-2-chloro-6-methyl-aniline, obtained as indicated in point (a) above, is treated as described in Example 3, Method (b), point (a) to obtain N-(β-chloropropyl)-2-chloro-6-methyl-aniline with a yield of 83.4%; b.p.: 106°–108° C./0.7 mm Hg.

(c) N-(β-Chloropropyl)-2-chloro-6-methyl-aniline, obtained is described in point (b) above, is reacted with 2,6-dimethylaniline as described in Example 16, point (c), and the free base is distilled under reduced pressure. 1-(2'-Chloro-6'-methyl-phenyl-amino)-2-(2',6'-dimethylphenyl-amino)-propane is obtained with a yield of 24.2%; b.p.: 177°–180° C./0.4 mm Hg.

EXAMPLE 27

1,3-Bis(4'-chlorophenyl)-2-imino-4-methyl-imidazolidine

M.p.: 117°–119° C.; yield: 76.5%.

1,2-Bis(4'-chlorophenyl-amino)-propane, applied as starting substance, is prepared as follows:

(a) 4-Chloroaniline is reacted with 1,2-epoxypropane as described in Example 3, Method (b), point (a) to obtain N-(β-hydroxypropyl)-4-chloro-aniline with a yield of 61.0%; b.p.: 158°–164° C./0.3 mm Hg.

(b) N-(β-Hydroxypropyl)-4-chloro-aniline, obtained as indicated in point (a) above, is treated as described in Example 3, Method (b), point (a) to obtain N-(β-chloropropyl)-4-chloro-aniline with a yield of 50.0%; b.p.: 120°–123° C./0.4 mm Hg.

(c) N-(β-Chloropropyl)-4-chloro-aniline, obtained as indicated in point (b) above, is reacted with 4-chloroaniline as described in Example 16, point (c) to obtain 1,2-bis(4'-chlorophenyl-amino)-propane with a yield of 84.9%. The product melts at 77°–80° C.

EXAMPLE 28

1-(2',6'-Dimethylphenyl)-2-imino-3-(4'-chlorophenyl)-4-methyl-imidazolidine

M.p.: 168°–171° C. (fumarate); yield: 64.1%.

1-(2',6'-Dimethylphenyl-amino)-2-(4'-chlorophenylamino)-propane, applied as starting substance, is prepared as follows:

A mixture of 28.2 g (0.143 moles) of N-(β-chloropropyl)-2,6-dimethylaniline, prepared as described in Example 3, Method (b), point (a), 36.4 g (0.285 moles) of 4-chloroaniline and 1.6 g (10 mmoles) of potassium iodide is stirred at 140° to 145° C. for 3 hours under nitrogen atmosphere. The mixture is allowed to cool to about 60° C., and 30 ml of ethyl acetate are added. The mixture is cooled to room temperature, and the separated precipitate is filtered off, washed with ethyl acetate and dried. 14.0 g of 1-(2',6'-dimethyl-phenylamino)-2-(4'-chlorophenyl-amino)-propane hydrochloride (fraction A) are obtained. The filtrate is acidified with isopropanolic hydrochloric acid (acid content: about 15 g/100 ml), the separated precipitate is filtered off, washed with isopropanol and dried. 28.8 g of the same compound (fraction B) are obtained. Fractions A and B are combined, triturated with 100 ml of water, filtered, washed with water, dried, and the resulting solid, weighing 25.7 g, is recrystallized from methanol. 21.4 g (46.0%) of pure 1-(2',6'-dimethylphenylamino)-2-(4'-chlorophenyl-amino)-propane hydrochloride are obtained; m.p.: 170°–176° C. This salt is converted to the free base as described in Example 3, Method (b), point (b), and the base is separated by extracting the reaction mixture with chloroform.

EXAMPLE 29

1-(4'-Chlorophenyl)-2-imino-3-(2',6'-dimethylphenyl)-4-methyl-imidazolidine

M.p.: 155°–157° C. (difumarate); yield: 43.9%.

1-(4'-Chlorophenyl-amino)-2-(2',6'-dimethyl-phenylamino)-propane, applied as starting substance, is obtained with a yield of 50.9% by reacting N-(β-chlorophenyl)-4-chloro-aniline, a compound prepared as described in Example 27, point (b), with 2,6-dimethylaniline according to the method given in Example 25, point (a). The hydrochloride of the product melts at 170°–178° C.

EXAMPLE 30

1-(2',3'-Dimethylphenyl)-2-imino-3-(4'-chlorophenyl)-4-methyl-imidazolidine

M.p.: 82°–84° C.; yield: 82.6%.

1-(2',3'-Dimethylphenyl-amino)-2-(4'-chlorophenylamino)-propane, applied as starting substance, is prepared as follows: N-(β-bromopropyl)-2,3-dimethylaniline, obtained as described in Example 13, point (b), is reacted with 4-chloroaniline. The reaction is performed as described in Example 3, Method (c), point (b) with the difference that isopropanolic hydrochloric acid is substituted for aqueous hydrochloric acid. The resulting hydrochloride, melting at 147°–151° C., is treated as described in Example 6, point (a) to obtain the free base with a yield of 35.9%; m.p.: 55°–58° C.

EXAMPLE 31

1-(2',6'-Dimethylphenyl)-2-imino-3-phenyl-4-methylimidazolidine

M.p.: 190°–195° C. (hydrobromide); yield: 52.3%.

1-(2',6'-Dimethylphenyl)-2-phenyl-amine-propane, applied as starting substance, is prepared with a yield of 41.0% by reacting N-(β-bromopropyl)-2,6-dimethyl-aniline, a compound obtained as described in Example 3, Method (c), point (a), with aniline according to the process given in Example 3, Method (c), point (b). The boiling point of the product is 116°–120° C./1.5 mm Hg.

EXAMPLE 32

1,3-Bis(2',6'-dimethylphenyl)-2-methylimino-imidazolidine

Method (a)

3.0 g of yellow mercury(II)oxide are added to a solution of 3.4 g (10 moles) of 1-methyl-3-(2',6'-dimethyl-phenyl)-3-(β-/2',6'-dimethylphenyl-amino/-ethyl)-thiourea in 50 ml of xylene, and the mixture is boiled for one hour. The mixture is cooled, the inorganic precipitate is filtered off, and the filtrate is evaporated in vacuo. The residue is triturated with n-hexane. The separated precipitate is filtered off, washed with n-hexane and dried at 40° to 50° C. 2.23 g (72.6%) of 1,3-bis(2',6'-dimethylphenyl)-2-methylimino-imidazolidine are obtained: m.p.: 180°–181° C.

1-Methyl-3-(2',6'-dimethylphenyl)-3-(β-/2',6'-dimethylphenyl-amino/-ethyl)-thiourea, applied as starting substance, is prepared as follows:

A mixture of 10.0 g (37.2 mmoles) of 1,2-bis(2',6'-dimethylphenyl-amino)-ethane, 2.9 g (39.7 mmoles) of methyl isothiocyanate and 100 ml of chloroform is boiled for 20 hours, and thereafter the solvent is evaporated under reduced pressure. The residual thick oil crystallizes upon standing. After trituration with cyclohexane 9.41 g (74.1%) of 1-methyl-3-(2',6'-dimethyl-phenyl)-3-(β-/2',6'-dimethylphenyl/aminoethyl)-thiourea are obtained; m.p.: 103°–105° C.

Method (b)

A mixture of 8.3 g (28.3 mmoles) of 1,3-bis(2',6'-dimethylphenyl)-2-imino-imidazolidine, prepared as described in Example 1, Method (a), 150 ml of methyl-ethyl-ketone, 10.0 g (0.1 moles) of potassium hydrogen-carbonate and 1.85 ml (4.26 g, 30 mmoles) of methyl iodide is stirred at room temperature for 8 hours. The separated precipitate is filtered off, and the filtrate is evaporated in vacuo. The residue is combined with the precipitate obtained with the previous operation, suspended in 150 ml of water, allowed to stand for 2 hours, and then the insolubles are filtered off. 10.15 g (82.4%) of crude 1,3-bis(2',6'-dimethylphenyl)-2-methylimino-imidazolidine hydroiodide are obtained.

The crude salt is dissolved in 300 ml of methanol, 100 ml of Amberlite IRA 410 anion exchange resin (chloride cycle) are added, and the mixture is stirred at room temperature for 8 hours. The resin is filtered off, washed with methanol, and the filtrate is evaporated under reduced pressure. The resulting 6.7 g (69.1%) of crude hydrochloride is recrystallized from a mixture of isopropanol and ethyl acetate to obtain 1,3-bis(2',6'-dimethylphenyl)-2-methylimino-imidazolidine hydrochloride as colourless crystals melting at 307°–308° C.

The compounds listed in Examples 33 and 34 are prepared as described in Example 32, Method (b), utilizing appropriately substituted compounds of the general formula (I), wherein $R^6$ is hydrogen, as starting substances.

EXAMPLE 33

1,3-Bis(2',6'-dimethylphenyl)-2-methylimino-4-methyl-imidazolidine

The title compound, melting at 98°–100° C., is obtained with a yield of 81.7% from 1,3-bis(2',6'-dimethyl-phenyl)-2-imino-4-methyl-imidazolidine, prepared as described in Example 3.

EXAMPLE 34

1,3-Bis(2',6'-dimethylphenyl)-2-methylimino-hexahydro-pyrimidine

The title compound is obtained with a yield of 67.4% from 1,3-bis(2',6'-dimethylphenyl)-2-imino-hexahydro-pyrimidine, prepared as described in Example 2. The hydrochloride of the product melts at 146°–150° C.

EXAMPLE 35

1,3-Bis(2',6'-dimethylphenyl)-2-(β,β,β-trifluoroethyl)-imino-4-methyl-imidazolidine 6.15 g (20 mmoles) of 1,3-bis(2',6'-dimethylphenyl)-2-imino-4-methyl-imidazolidine, obtained as described in Example 3, are dissolved in 50 ml xylene. 2.81 g (10 mmoles) of (β,β,β-trifluoroethyl) trichloromethanesulfonate are added, and the mixture is boiled for 0.5 hours. The mixture is cooled, the separated precipitate is filtered off, washed with xylene and ethyl acetate, and dried. 2.7 g of the trichloromethanesulfonate of the starting substance are obtained; m.p.: 275°–277° C. The filtrate is evaporated under reduced pressure, and the residue is triturated with diethyl ether to obtain 1.45 g of a crystalline substance. The etheral mother liquor is partially evaporated to obtain further 1.0 g of the product. Thus a total amount of 2.45 g (43.1%, calculated for the converted starting substance) of 1,3-bis(2',6'-dimethylphenyl)-2-(β,β,β-trifluoroethyl)-imino-4-methyl-imidazolidine are obtained, m.p.: 105°–106° C.

EXAMPLE 36

1,3-Bis(2',6'-dimethylphenyl)-2-n-butyl-imino-4-methyl-imidazolidine

A solution of 6.0 g (19.5 mmoles) of 1,3-bis(2',6'-dimethylphenyl)-2-imino-4-methyl-imidazolidine, obtained as described in Example 3, and 3.3 g (24 mmoles) of n-butylbromide in 60 ml of dry dimethylformamide is stirred at 100° to 105° C. for 6 hours, and then the mixture is allowed to stand overnight. Next day the mixture is poured onto 300 ml of icy water, and shaken thrice with 50 ml of diethyl ether each in order to remove the impurities. Thereafter the aqueous phase is extracted thrice with 50 ml of chloroform each, the organic solutions are combined, dried over anhydrous potassium carbonate, filtered, and the filtrate is evaporated in vacuo. The residue, weighing 7.0 g, is recrystallized from ethyl acetate and then triturated with hot dioxane to obtain 3.9 g (45.0%) of 1,3-bis(2',6'-dimethylphenyl)-2-(n-butyl)-imino-4-methyl-imidazolidine hydrobromide, m.p.: 216°–218° C.

EXAMPLE 37

1,3-Bis(2',6'-dimethylphenyl)-2-formylimino-imidazolidine

A solution of 7.5 g (85 mmoles) of acetyl formate (a mixed anhydride of formic acid and acetic acid) in 30 ml of dry chloroform is added dropwise, at room temperature, to a solution of 5.0 g (17.0 mmoles) of 1,3-bis(2',6'-dimethylphenyl)-2-imino-imidazolidine, prepared as described in Method (a) of Example 1, in 50 ml of dry chloroform. The resulting mixture is stirred at 45° to 50° C. for 4 hours, thereafter it is cooled with ice, and 10 ml of a 10% aqueous sodium hydrogencarbonate solution are added dropwise to the stirred mixture at a temperature not exceeding +10° C. The aqueous phase is separated, the chloroform phase is washed thrice with 50 ml of water each, dried over anhydrous sodium sulfate, filtered, and the solvent is evaporated under reduced pressure, 4.6 g (84.2%) of 1,3-bis(2',6'-dimethylphenyl)-2-formylimino-imidazolidine are obtained; the product melts at 306°-308° C. after recrystallization from methanol.

EXAMPLE 38

1,3-Bis(2',6'-dimethylphenyl)-2-acetimino-imidazolidine

A mixture of 10.0 g (34.1 mmoles) of 1,3-bis(2',6'-dimethylphenyl)-2-imino-imidazolidine, prepared as described in Example 1, Method (a), and 100 ml of acetic anhydride is stirred and boiled for 2 hours. The excess of acetic anhydride is distilled off under reduced pressure, and the residue is dried. The obtained crude product, weighing 9.7 g (85.1%), is recrystallized from aqueous methanol to obtain pure 1,3-bis(2',6'-dimethylphenyl)-2-acetimino-imidazolidine, m.p.: 200°-201° C.

The compounds listed in Examples 39 and 40 are prepared by the method of Example 38, utilizing appropriately substituted compounds of the general formula (I), wherein $R^6$ is hydrogen, as starting substances.

EXAMPLE 39

1,3-Bis(2',6'-dimethylphenyl)-2-acetimino-4-methylimidazolidine

The title compound, melting at 181°-182.5° C., is obtained with a yield of 86.0% from 1,3-bis(2',6'-dimethylphenyl)-2-imino-4-methyl-imidazolidine, prepared as described in Example 3.

EXAMPLE 40

1,3-Bis(2',6'-dimethylphenyl)-2-acetimino-4-acetoxymethyl-imidazolidine

The title compound, melting at 163°-164° C., is obtained with a yield of 87.7% from 1,3-bis(2',6'-dimethylphenyl)-2-imino-4-hydroxymethyl-imidazolidine, prepared as described in Example 6.

EXAMPLE 41

1,3-Bis(2',6'-dimethylphenyl)-2-acetimino-4-hydroxymethyl-imidazolidine

A solution of 7.0 g (175 mmoles) of sodium hydroxide in 100 ml of ethanol is added in a single portion to a solution of 7.0 g (17.2 mmoles) of 1,3-bis(2',6'-dimethylphenyl)-2-acetimino-4-acetoxymethyl-imidazolidine, prepared as described in Example 40, in 50 ml of ethanol at room temperature. The reaction mixture is stirred at room temperature for one hour, thereafter it is poured into 300 ml of icy water, and extracted four times with 100 ml of chloroform each. The organic solutions are combined, washed thrice with 100 ml of water each, dried over anhydrous sodium sulfate, and the solvent is evaporated under reduced pressure. The residue is recrystallized from dioxane. 5.8 g (92.1%) of 1,3-bis(2',6'-dimethylphenyl)-2-acetimino-4-hydroxymethylimidaaolidine are obtained; m.p.: 194°-196° C.

EXAMPLE 42

1,3-Bis(2',6'-dimethylphenyl)-2-trifluoroacetimino-4-methyl-imidazolidine

A solution of 1.53 ml (2.31 g, 11 mmoles) of trifluoroacetic anhydride in 10 ml of dry benzene is added dropwise at 15° to 20° C. to a solution of 3.1 g (10 mmoles) of 1,3-bis(2',6'-dimethylphenyl)-2-imino-4-methylimidazolidine, prepared as described in Example 3, in 30 ml of dry benzene. The resulting mixture is stirred for one hour at room temperature. Thereafter the solution is washed thrice with 20 ml of water each, dried over anhydrous sodium sulfate, and the solvent is evaporated under reduced pressure. The residue is triturated with diethyl ether, the separated precipitate is filtered off, washed with cold diethyl ether, and dried. 1.15 g (28.5%) of 1,3-bis(2',6'-dimethylphenyl)-2-trifluoroacetylimino-4-methyl-imidazolidine are obtained; m.p.: 232°-235° C. 0.25 g (5.9%) of 1,3-bis(2',6'-dimethylphenyl)-2-imino-4-methyl-imidazolidine trifluoroacetate (m.p.: 145°-147° C.) and 1.55 g 29.0%) of 1,3-bis(2',6'-dimethylphenyl)-2-imino-4-methyl-imidazolidine-bis(trifluoroacetate) (m.p.: 89°-92° C.) are obtained from the ethereal mother liquor by fractional crystallization.

EXAMPLE 43

1,3-Bis(2',6'-dimethylphenyl)-2-benzoyliminoimidazolidine

A mixture of 1.0 g (3.4 mmoles) of 1,3-bis(2',6'-dimethylphenyl)-2-imino-imidazolidine, prepared as described in Example 1, Method (a), 10 ml of 1,2-dichloroethane, 0.33 ml (0.32 g, 4.0 mmole) of dry pyridine and 0.46 ml (0.56 g, 4.0 mmoles) of benzoyl chloride is heated on a steam bath for 2 hours. The cooled mixture is washed thrice with 10 ml of water each, thrice with 10 ml of 10% aqueous sodium hydrogencarbonate solution each, and again thrice with 10 ml of water each, dried over anhydrous sodium sulfate, and the solvent is evaporated under reduced pressure. 1.0 g (74.1%) of crude 1,3-bis(2',6'-dimethylphenyl)-2-benzoylimino-imidazolidine are obtained. After recrystallization from aqueous methanol the product melts at 176°-178° C.

The compounds listed in Examples 44 to 48 are prepared from the appropriately substituted compounds of the general formula (I), wherein $R^6$ is hydrogen, and the respective acyl chlorides, according to the method of Example 43.

EXAMPLE 44

1,3-Bis(2',6'-dimethylphenyl)-2-(p-chlorobenzoyl)-imino-imidazolidine

The title compound, melting at 155°-156° C., is prepared with a yield of 59.6% from 1,3-bis(2',6'-dimethylphenyl)-2-imino-imidazolidine, obtained as described in Example 1, Method (a).

EXAMPLE 45

1,3-Bis(2',6'-dimethylphenyl)-2-(p-chlorobenzoyl)-imino-4-methyl-imidazolidine

The title compound, melting at 128°–130° C., is obtained with a yield of 73.7% from 1,3-bis(2',6'-dimethylphenyl)-2-imino-4-methyl-imidazolidine, prepared as described in Example 3.

EXAMPLE 46

1,3-Bis(2',6'-dimethylphenyl)-2-(p-chlorobenzoyl)-imino-hexahydro-pyrimidine

The title compound, melting at 229°–230° C., is obtained with a yield of 60.0% from 1,3-bis(2',6'-dimethylphenyl)-hexahydro-pyrimidine, prepared as described in Example 2.

EXAMPLE 47

1,3-Bis(2',6'-dimethylphenyl)-2-(1'-adamantoyl)-imino-imidazolidine

The title compound, melting at 261°–263° C., is obtained with a yield of 40.1% from 1,3-bis(2',6'-dimethylphenyl)-2-imino-imidazolidine, prepared as described in Example 1, Method (a).

EXAMPLE 48

1,3-Bis(2',6'-dimethylphenyl)-2-benzenesulfonyl-imino-imidazolidine

The title compound, melting at 223°–224.5° C., is obtained with a yield of 65.5% from 1,3-bis(2',6'-dimethylphenyl)-2-imino-imidazolidine, prepared as described in Example 1, Method (a).

EXAMPLE 49

1,3-Bis(2',6'-dimethylphenyl)-2-carbethoxyimino-4-methyl-imidazolidine

A solution of 1.0 ml (1.38 g, 10.5 mmoles) of ethyl chloroformate in 10 ml of dry benzene is added dropwise at room temperature to a stirred solution of 6.15 g (20 mmoles) of 1,3-bis(2',6'-dimethylphenyl)-2-imino-4-methyl-imidazolidine, obtained as described in Example 7, in 60 ml of dry benzene. The mixture is stirred for additional 5 hours at room temperature, and then washed thrice with 50 ml of water each. The benzene solution is dried over anhydrous sodium sulfate, and the solvent is evaporated under reduced pressure. The thick, yellow oily residue is crystallized from diisopropyl ether to obtain 2.7 g (71.2%) of 1,3-bis(2',6'-dimethylphenyl)-2-carbethoxyimino-4-methyl-imidazolidine; m.p.: 124°–125° C.

The compounds listed in Examples 50 to 59 are prepered from the appropriately substituted compounds of the general formula (I), wherein $R^6$ is hydrogen, by the method described in Example 49.

EXAMPLE 50

1,3-Bis(2',6'-dimethylphenyl)-2-carbethoxyiminohexahydro-pyrimidine

The title compound is prepared from 1,3-bis(2',6'-dimethylphenyl)-2-imino-hexahydro-pyrimidine, obtained as described in Example 2.

EXAMPLE 51

1,3-Bis(2',6'-dimethylphenyl)-2-carbethoxyimino-4-methyl-hexahydro-pyrimidine

The title compound is prepared from 1,3-bis(2',6'-dimethylphenyl)-2-imino-4-methyl-hexahydro-pyrimidine, obtained as described in Example 8.

EXAMPLE 52

1,3-Bis(2',6'-dimethylphenyl)-2-carbethoxyiminoimidazolidine

The title compound is prepared from 1,3-bis(2',6'-dimethylphenyl)-2-imino-imidazolidine, obtained as described in Example 1, Method (a).

EXAMPLE 53

1,3-Bis(2',6'-dimethylphenyl)-2-carbethoxyimino-4,5-cis-dimethyl-imidozolidine

The title compound is prepared from 1,3-bis-(2',6'-dimethylphenyl)-2-imino-4,5-cis-dimethyl-imidazolidine, prepared as described in Example 10.

EXAMPLE 54

1,3-Bis(2',6'-dimethylphenyl)-2-carbethoxyimino-4,5-trans-dimethyl-imidazolidine The title compound is prepared from 1,3-bis(2',6'-dimethylphenyl)-2-imino-4,5-trans-dimethyl-imidazolidine, obtained as described in Example 11.

EXAMPLE 55

1,3-Bis(2',6'-dimethylphenyl)-2-carbethoxyimino-4,4-dimethyl-imidazolidine

The title compound is prepared from 1,3-bis(2',6'-dimethylphenyl)-2-imino-4,4-dimethyl-imidazolidine, obtained as described in Example 9.

EXAMPLE 56

1,3-Bis(2',3'-dimethylphenyl)-2-carbethoxyimino-4-methyl-imidazolidine

The title compound is prepared from 1,3-bis(2',3'-dimethylphenyl)-2-imino-4-methyl-imidazolidine, obtained as described in Example 13.

EXAMPLE 57

1,3-Bis(2',6'-dimethylphenyl)-2-carbethoxyimino-4-hydroxymethyl-imidazolidine

The title compound is prepared from 1,3-bis(2',6'-dimethylphenyl)-2-imino-4-hydroxymethyl-imidazolidine, obtained as described in Example 6.

EXAMPLE 58

1,3-Bis(4'-chlorophenyl)-2-carbethoxyimino-4-methyl-imidazolidine

The title compound is prepared from 1,3-bis(4'-chlorophenyl)-2-imino-4-methyl-imidazolidine, obtained as described in Example 27.

EXAMPLE 59

1,3-Bis(4'-methoxyphenyl)-2-carbethoxyimino-4-methylimidazolidine

The title compound is prepared from 1,3-bis(4'-methoxyphenyl)-2-imino-4-methyl-imidazolidine, obtained as described in Example 21.

The compounds listed in Examples 60 and 61 are prepared as described in Example 49, with the difference that ethyl chloroformate is replaced by the appropriate other chloroformates.

EXAMPLE 60

1,3-Bis(2',6'-dimethylphenyl)-2-phenoxycarbonylimino-4-methyl-imidazolidine

The title compound, melting at 165°–166° C., is prepared with a yield of 61.2% from 1,3-bis(2',6'-dimethylphenyl)-2-imino-4-methyl-imidazolidine, obtained as described in Example 3, and phenyl chloroformate.

EXAMPLE 61

1,3-Bis(2',6'-dimethylphenyl)-2-benzyloxycarbonylimino-4-methyl-imidazolidine

The title compound, melting at 74°–75° C., is prepared with a yield of 43.4% from 1,3-bis(2',6'-dimethylphenyl)-2-imino-4-methyl-imidazolidine, obtained as described in Example 3, and benzyl chloroformate.

EXAMPLE 62

1,3-Bis(2',6'-dimethylphenyl)-2-(tert.-butoxycarbonyl)-imino-4-methyl-imidazolidine 20 mmoles of tert.-butoxycarbonyl azide are added to a solution of 5.9 g (19.2 mmoles) of 1,3-bis(2',6'-dimethylphenyl)-2-imino-4-methyl-imidazolidine, obtained as described in Example 3, in 60 ml of dimethylformamide, and the resulting mixture is stirred at 100° to 105° C. for 3 hours. The mixture is cooled, poured onto 200 ml of icy water, and extracted thrice with 80 ml of diethyl ether each. The etheral solutions are combined, washed twice with 50 ml of water each, twice with 50 ml of 1% aqueous acetic acid solution each, and again twice with 50 ml of water each. The solution is dried over anhydrous magnesium sulfate, and the solvent is evaporated under reduced pressure. The yellow, sticky, solid residue is purified by triturating it with diisopropyl ether, and the resulting 1.51 g of crude product is recrystallized from diisopropyl ether. The obtained 1,3-bis(2',6'-dimethylphenyl)-2-(tert.-butoxycarbonyl)-imino-4-methyl-imidazolidine melts at 158°–159° C.

The aqueous and aqueous acetic acidic washings are combined, rendered alkaline, and the separated solid is filtered off. 3.3 g of the starting 1,3-bis(2',6'-dimethylphenyl)-2-imino-4-methyl-imidazolidine are recovered. Thus the product is obtained with a yield of 43.7% calculated for the converted starting substance.

EXAMPLE 63

1,3-Bis(2',6'-dimethylphenyl)-2-acetimino-imidazolidine-4-carboxylic acid

A solution of 1.0 g (25 mmoles) of sodium hydroxide in 250 ml of water is added to a suspension of 5.0 g (13.7 mmoles) of 1,3-bis(2',6'-dimethylphenyl)-2-acetimino-4-hydroxymethyl-imidazolidine, obtained as described in Example 41, in 150 ml of dioxane. 11.0 g (69.6 mmoles) of solid potassium permangenate are added to the mixture in small portions, within about 4 hours, at room temperature, and the resulting mixture stirred for additional 2 hours at room temperature. Thereafter the mixture is allowed to stand at room temperature overnight. Next day the separated manganese dioxide is filtered off, washed with water, and the filtrate is extracted thrice with 100 ml of chloroform each. The chloroform solutions are combined, dried over anhydrous sodium sulfate, and the solvent is evaporated under reduced pressure. In this way 1.05 g (21.0%) of unreacted starting substance are recovered. The pH of the extracted aqueous phase is adjusted to 4 with 20% aqueous hydrochloric acid, and the acidic solution is extracted thrice with 100 ml of chloroform each. The organic solutions are combined, dried over anhydrous sodium sulfate, the solvent is evaporated under reduced pressure, and the residue is triturated with diethyl ether. The separated precipitate is filtered off, washed with diethyl ether, and dried. 3.0 g (57.7% or, calculated for the converted starting substance, 73.2%) of 1,3-bis(2',6'-dimethylphenyl)-2-acetimino-imidazolidine-4-carboxylic acid are obtained. This crude product, melting at 210°–217° C., is sufficiently pure to subject it to subsequent reactions.

EXAMPLE 64

Methyl 1,3-bis(2',6'-dimethylphenyl)-2-acetiminoimidazolidine-4-carboxylate

Etheral diazomethane solution is added at room temperature to a solution of 0.3 g (0.79 mmoles) of 1,3-bis(2',6'-dimethylphenyl)-2-acetimino-imidazolidine-4-carboxylic acid, obtained as described in Example 63, in 5 ml of methanol until a persistent yellow colour appears. After 15 minutes of standing the solvents are evaporated under reduced pressure, and the residue is crystallized from a mixture of ethyl acetate and n-hexane. 0.17 g (54.8%) of methyl 1,3-bis(2',6'-dimethylphenyl)-2-acetimino-imidazolidine-4-carboxylate are obtained; m.p.: 145°–148° C.

EXAMPLE 65

1,3-Bis(2',6'-dimethylphenyl)-2-imino-imidazolidine-4-carboxylic acid

A mixture of 8.0 g (21.1 mmoles) of 1,3-bis(2',6'-dimethylphenyl)-2-acetimino-imidazolidine-4-carboxylic acid, obtained as described in Example 63, and 200 ml of 1 n aqueous hydrochloric acid is heated on a steam bath for 3 hours, and then the mixture is allowed to stand at +5° C. overnight. Next day the separated precipitate is filtered off, washed with cold 1 n aqueous hydrochloric acid, and dried. 2.2 g of 1,3-bis(2',6'-dimethylphenyl)-2-imino-imidazolidine-4-carboxylic acid hydrochloride are obtained. This crude salt, melting at 288°–292° C., is sufficiently pure to subject it to further reactions. After recrystallization from 1 n aqueous hydrochloric acid the product melts at 316°–318° C. The aqueous acidic solution is concentrated to obtain further 4.4 g of the product (m.p.: 246°–256° C.), which is recrystallized from 1 n aqueous hydrochloric acid to obtain 2.9 g of a practically pure substance, melting at 292°–296° C. The pure compound is obtained with a total yield of 71.8%.

EXAMPLE 66

Methyl 1,3-bis(2',6'-dimethylphenyl)-2-imino-imidazolidine-4-carboxylate

Dry, gaseous hydrochloric acid is introduced into a solution of 1.7 g (4.55 mmoles) of 1,3-bis(2,',6'-dimethylphenyl)-2-imino-imidazolidine-4-carboxylic acid hydrochloride, obtained as described in Example 65, in 20 ml of dry methanol at 0° to +5° C. After one hour the introduction of the gas is stopped, and the mixture is allowed to stand at +5° C. for 24 hours. The fluffy insolubles floating in the solution are filtered off, and the solvent is evaporated in vacuo. The residue is triturated with dry diethyl ether, the separated precipitate is filtered off, washed with diethyl ether, and dried, 1.6 g (90.9%) of 1,3-bis(2',6'-dimethylphenyl)-2-imino-imidazolidine-4-carboxylic acid methylester hydrochloride are obtained as a colourless, hygroscopic crystalline substance; m.p.: 113°-115° C. (in sealed tube).

EXAMPLE 67

(β-Hydroxyethyl) 1,3-bis(2',6'-dimethylphenyl)-2-imino-imidazolidine-4-carboxylate One proceeds as described in Example 66 with the difference that ethylene glycol is substituted for methanol. (β-Hydroxyethyl) 1,3-bis(2',6'-dimethylphenyl)-2-imino-imidazolidine-4-carboxylate hydrochloride is obtained with a yield of 82.2%; m.p.: 109°-110° C. (in sealed tube).

EXAMPLE 68

1,3-Bis(2',6'-dimethylphenyl)-2-cyanimino-4-methylimidazolidine

A solution of 3.6 g (34.2 mmoles) of cyanogen bromide in 40 ml of benzene is added dropwise, within 0.5 hours, to a solution of 20.0 g (65.1 mmoles) of 1,3-bis(2',6'-dimethylphenyl)-2-imino-4-methyl-imidazolidine, obtained as described in Example 3, in 200 ml of benzene under stirring and cooling with water. The resulting mixture is stirred for additional 5 hours at room temperature, and then allowed to stand overnight. Next day the precipitate is filtered off, washed with benzene and dried. In this way 31.7 mmoles (48.7%) of the starting substance are recovered as the respective hydrobromide. The benzene filtrate is washed thrice with 50 ml of water each, dried over anhydrous sodium sulfate, and the solvent is evaporated under reduced pressure. The resulting 7.85 g of beige, crystalline residue is recrystallized from isopropanol to obtain 6.4 g (29.4%, or, calculated for the converted starting substance, 57.7%) of pure 1,3-bis(2',6'-dimethylphenyl)-2-cyanimino-4-methyl-imidazolidine; m.p.: 243°-246° C.

The compounds listed in Examples 69 to 71 are prepared from the appropriately substituted compounds of the general formula (I), wherein $R^6$ is hydrogen, according to the method of Example 68.

EXAMPLE 69

1,3-Bis(2',6'-dimethylphenyl)-2-cyanimino-imidazolidine

The title compound, melting at 340°-342° C., is prepared with a yield of 42.7% from 1,3-bis(2',6'-dimethylphenyl)-2-imino-imidazolidine, obtained as described in Example 1, Method (a).

EXAMPLE 70

1,3-Bis(2',6'-dimethylphenyl)-2-cyanimino-4-hydroxymethyl-imidazolidine

The title compound, melting at 199°-201° C., is prepared with a yield of 16.9% from 1,3-bis(2',6'-dimethylphenyl)-2-imino-4-hydroxymethyl-imidazolidine, obtained as described in Example 6. The reaction is performed in ethanol, and the crude product is purified by column chromatography on silica gel, applying a 120:6:20:11 mixture of ethyl acetate, cetic acid, pyridine and water as eluting agent.

EXAMPLE 71

1,3-Bis(2',3'-dimethylphenyl)-2-cyanimino-imidazolidine

The title compound, melting at 203°-205° C., is prepared with a yield of 87.4% from 1,3-bis(2',3'-dimethylphenyl)-2-imino-imidazolidine, obtained as described in Example 12.

EXAMPLE 72

1-(1',3'-Bis/2'',6''-dimethylphenyl/-4'-methyl-imidazolidine-2'-ylidene)-urea

A mixture of 6.4 g (19.3 mmoles) of 1,3-bis(2',6'-dimethylphenyl)-2-cyanimino-4-methyl-imidazolidine, obtained as described in Example 68, 60 ml of ethanol and 2.0 ml of concentrated hydrochloric acid is boiled for 4 hours. Thereafter the mixture is poured onto 200 ml of icy water and allowed to stand overnight. The insolubles are filtered off, washed with water, the filtrate is neutralized (pH=7 to 7.5) with 10% aqueous sodium hydrogencarbonate solution, and the neutral aqueous phase is extracted thrice with 100 ml of chloroform each. The chloroform solutions are combined, washed thrice with 50 ml of water each, dried over anhydrous sodium sulfate, and the solvent is evaporated under reduced pressure. The residue is triturated with 20 ml of cyclohexane, the separated precipitate is filtered off, washed with cyclohexane, and dried, 4.0 g (59.2%) of 1-(1',3'-bis/2'',6''-dimethylphenyl/-4'-methyl-imidazolidine-2'-ylidene)-urea are obtained; m.p.: 117°-120° C.

EXAMPLE 73

1-(1',3'-Bis/2'',6''-dimethylphenyl/-4'-methyl-imidazolidine-2'-ylidene)-3-methyl-urea 0.5 g (8.6 mmoles) of methyl isocyanate are added to a solution of 2.0 g (6.5 mmoles) of 1,3-bis(2',6'-dimethylphenyl)-2-imino-4-methyl-imidazolidine, obtained as described in Example 3, in 30 ml of dry chloroform, and the resulting mixture is boiled for 1 hour. The solution is cooled, washed thrice with 10 ml of water each, dried over anhydrous potassium carbonate, and the solvent is evaporated under reduced pressure. The residue is triturated with hot cyclohexane, the mixture is allowed to cool, thereafter the separated precipitate is filtered off, washed with cyclohexane and dried. 1.83 g (77.2%) of 1-(1',3'-bis/2'',6''-dimethylphenyl/-4'-methyl-imidazolidine-2'-ylidene)-3-methyl-urea are obtained; m.p.: 153°-155° C.

EXAMPLE 74

1,3-Bis(2',6'-dimethylphenyl)-2-acetimino-4-chloromethyl-imidazolidine 5.4 g (42.1 mmoles) of freshly prepared solid chloromethylene-dimethyl-ammonium chloride (see D. R. Hepburn and H. R. Hudson, J. Chem. Soc., Perkin I. 7976, 154) are added in some portions, within about 5 minutes, to a suspension of 10.2 g (27.9 mmoles) of 1,3-bis(2',6'-dimethylphenyl)-2-acetimino-4-hydroxymethyl-imidazolidine, obtained as described in Example 41, in 100 ml of dry acetonitrile at room temperature. The reaction mixture is boiled for 3 hours, and then allowed to stand overnight. The solution is concentrated to a final volume of about 30 ml, this concentrate is diluted with 200 ml of water, rendered alkaline with 2 n aqueous ammonia, and extracted thrice with 100 ml of chloroform each. The chloroform solutions are combined, washed thrice with 50 ml of water each, dried over anhydrous potassium carbonate, and the solvent is evaporated. The residue is triturated with 30 ml of diethyl ether to obtain 8.0 g (74.7%) of 1,3-bis(2',6'-dimethylphenyl)-2-acetimino-4-chloromethyl-imidazolidine. This crude product, melting at 142°–145° C., is sufficiently pure to subject it to further conversions. After recrystallization from cyclohexane the product melts at 147°–149° C.

EXAMPLE 75

1,3-Bis(2',6'-dimethylphenyl)-2-acetimino-4-chloromethyl-imidazolidine 7.2 ml (11.9 g, 100 mmoles) of thionyl chloride are added dropwise to a stirred mixture of 30.0 g (82.1 mmoles) of 1,3-bis(2',6'-dimethylphenyl)-2-acetimino-4-hydroxymethylimidazolidine, obtained as described in Example 41, 300 ml of 1,2-dichloroethane and 6.3 ml (82.1 mmoles) of dimethylformamide at room temperature. The mixture is stirred for additional 3 hours at room temperature, thereafter it is cooled with ice, and 50 ml of water, followed by 50 ml of 2 n aqueous sodium hydroxide solution, are added dropwise. The organic phase is separated, washed twice with 50 ml of water each, dried over anhydrous potassium carbonate, and the solvent is evaporated under reduced pressure. The solid residue is extracted several times with hot cyclohexane. The cyclohexane solutions are combined and allowed to cool. The separated precipitate is filtered off, washed with cyclohexane and dried. 18.0 g (57.1%) of 1,3-bis(2',6'-dimethylphenyl)-2-acetimino-4-chloromethyl-imidazolidine are obtained; m.p.: 140°–145° C.

EXAMPLE 76

1,3-Bis(2',6'-dimethylphenyl)-2-imino-4-chloromethyl-imidazolidine

A mixture of 4.0 g (10.4 mmoles) of 1,3-bis(2',6'-dimethylphenyl)-2-acetimino-4-chloromethyl-imidazolidine, obtained as described in Example 74, and 20 ml of 20% aqueous hydrochloric acid is heated on a steam bath for 1.5 hours. The solvent is evaporated under reduced pressure, 20 ml of ethanol are added to the residue, and the mixture is evaporated. This latter operation is repeated once again. The residue is crystallized from a mixture of dry acetone and diisopropyl ether to obtain 3.55 g (90.3%) of 1,3-bis(2',6'-dimethylphenyl)-2-imino-4-chloromethyl-imidazolidine hydrochloride; m.p.: 296°–298° C. (in sealed tube; decomposition).

EXAMPLE 77

1,3-Bis(2',6'-dimethylphenyl)-2-imino-4-carboxamidomethyl-imidazolidine

A mixture of 4.0 g (81.6 mmoles) of sodium cyanide, 80 ml of dry dimethylsulfoxide and 3.1 g (8.1 mmoles) of 1,3-bis(2',6'-dimethylphenyl)-2-acetimino-4-chloromethyl-imidazolidine, obtained as described in Example 74, is stirred at 100° to 105° C. or one hour. The mixture was cooled, poured onto 200 ml of ice water, and allowed to stand overnight. Next day the separated precipitate is filtered off, washed with water and dried. 2.8 g (98.6%) of 1,3-bis(2',6'-dimethylphenyl)-2-imino-4-carboxamidomethyl-imidazolidine are obtained. This crude product, melting at 90°–96° C., is sufficiently pure to subject it to further reactions. After recrystallization from isopropanol the product melts at 100°–102° C.

EXAMPLE 78

1,3-Bis(2',6'-dimethylphenyl)-2-acetimino-4-cyanomethyl-imidazolidine

A mixture of 0.15 g (0.43 mmoles) of 1,3-bis(2',6'-dimethylphenyl)-2-imino-4-carboxamidomethyl-imidazolidine, obtained as described in Example 77, and 3 ml of acetic anhydride is boiled for 2 hours. The reaction mixture is cooled, poured into 30 ml of water, and the resulting mixture is extracted thrice with 20 ml of chloroform each. The organic solutions are combined, washed thrice with 10 ml of water each, dried over anhydrous potassium carbonate, and the solvent is evaporated under reduced pressure. The solid residue is recrystallized from isopropanol to obtain 0.15 g (93.3%) of 1,3-bis(2',6'-dimethylphenyl)-2-acetimino-4-cyanomethyl-imidazolidine; m.p.: 138°–141° C.

EXAMPLE 79

1,3-Bis(2',6'-dimethylphenyl)-2-imino-imidazolidine-4-acetic acid

A mixture of 2.2 g (6.3 mmoles) of 1,3-bis(2',6'-dimethylphenyl)-2-imino-4-carboxamidomethyl-imidazolidine, obtained as described in Example 77, and 20 ml of concentrated hydrochloric acid is heated on a steam bath for 0.5 hours. The solution is cooled, washed thrice with 10 ml of chloroform each, and the aqueous phase is evaporated under reduced pressure. The solid residue, weighing 1.55 g, is dissolved in 30 ml of acetonitrile, the solution is filtered, and the solvent is evaporated under reduced pressure. The residue is crystallized by triturating it with diisopropyl ether. 1.2 g (46.9%) of 1,3-bis(2',6'-dimethylphenyl)-2-imino-imidazolidine-4-acetic acid hydrochloride monohydrate are obtained, m.p.: 134°–138° C.

When the above product is allowed to stand at room temperature in ethyl acetate for 2 days, a transesterification reaction occurs, and ethyl 1,3-bis(2',6'-dimethylphenyl)-2-imino-imidazolidine-4-acetate, melting at 142°–144° C., is obtained.

EXAMPLE 80

(β-Hydroxyethyl) 1,3-bis(2',6'-dimethylphenyl)-2-imino-imidazolidine-4-acetate hydrochloride One proceeds as described in Example 57, with the difference that 1,3-bis(2',6'-dimethylphenyl)-2-imino-imidazolidine-4-acetic acid hydrochloride monohydrate, obtained according to Example 79, is applied as starting substance. (β-Hydroxyethyl) 1,3-bis(2',6'-dimethylphenyl)-2-imino-imidazolidine-4-acetate hydrochloride, melting at 106°–109° C., is obtained with a yield of 91.0%.

EXAMPLE 81

1,3-Bis(2',6'-dimethylphenyl)-2-imino-4-acetoxymethyl-imidazolidine

A solution of 5.4 g (16.7 mmoles) of 1,3-bis(2',6'-dimethylphenyl)-2-imino-4-hydroxymethyl-imidazolidine, obtained as described in Example 6, in 60 ml of methanol is acidified to pH=3 with isopropanolic hydrochloric acid (acid content: about 15 g/100 ml), and then the solvents are evaporated under reduced pressure. 6.0 g (100%) of the respective hydrochloride are obtained; m.p.: 219°–220° C.

This salt is dissolved in 40 ml of dry dimethylformamide, 2.45 ml (1.82 g, 18 mmoles) of dry triethylamine are added, and 1.30 ml (1.43 g, 18.2 mmoles) of acetyl chloride are added dropwise to the mixture at a temperature between 0° C. and +5° C. The reaction mixture is stirred for one hour at this temperature and for an additional hour at a temperature between −20° C. and −15° C., the separated triethylamine hydrochloride is filtered off, and washed with a small amount of cold dimethylformamide. 2.1 g (85.0%) of the salt are obtained. The filtrate is evaporated under reduced pressure, and the oily residue is triturated with ethyl acetate. The separated crystalline substance is filtered off, washed with ethyl acetate and dried. 6.1 g (91.0%) of 1,3-bis(2',6'-dimethylphenyl)-2-imino-4-acetoxymethyl-imidazolidine hydrochloride are obtained; m.p.: 184°–186° C. After recrystallization from isopropanol the product melts at 187°–188° C.

EXAMPLE 82

1,3-Bis(2',6'-dimethylphenyl)-2-acetimino-4-bromomethyl-imidazolidine 5.0 g (13.7 mmoles) of 1,3-bis(2',6'-dimethylphenyl)-2-acetimino-4-hydroxymethyl-imidazolidine, obtained as described in Example 41, are added in a single portion to a stirred solution of 4.45 g (20.5 mmoles) of bromomethylene-dimethyl-ammonium bromide (see D. R. Hepburn and H. R. Hudson, loc. cit.) in 50 ml of dry acetonitrile at room temperature. A homogeneous, yellow solution is being formed within some seconds, and after about 1 minute a colorless precipitate starts to separate from the mixture. The reaction mixture is stirred and boiled for 3 hours and then allowed to stand overnight. Next day the precipitate is filtered off, washed with acetonitrile and dried. In this way 6.5 mmoles (47.4%) of the starting substance are recovered as the hydrobromide. The acetonitrile filtrate is diluted with 100 ml of water, 50 ml of chloroform are added, and the mixture is rendered alkaline with 2 n aqueous sodium hydroxide solution. The aqueous phase is separated and extracted twice with 50 ml of chloroform each. The organic solutions are combined, washed thrice with 30 ml of water each, dried over anhydrous potassium carbonate, and the solvent is evaporated. The obtained sticky, solid residue is recrystallized from diisopropyl ether to obtain 1.7 g (29.0%, or, calculated for the converted starting substance, 55.1%) of 1,3-bis(2',6'-dimethylphenyl)-2-acetimino-4-bromomethyl-imidazolidine; m.p.: 171°–174° C.

EXAMPLE 83

1,3-Bis(2',6'-dimethylphenyl)-2-imino-bromomethyl-imidazolidine

One proceeds as described in Example 66, with the difference that 1,3-bis(2',6'-dimethylphenyl)-2-acetimino-4-bromomethyl-imidazolidine, obtained as described in Example 81, is applied as starting substance, and 1 n aqueous hydrochloric acid is substituted for the 20% aqueous hydrochloric acid. 1,3-Bis(2',6'-dimethylphenyl)-2-imino-4-bromomethyl-imidazolidine hydrochloride is obtained with a yield of 91.3%; m.p.: 116°–118° C. (decomposition).

EXAMPLE 84

(+)-1,3-Bis(2',6'-dimethylphenyl)-2-imino-4-methyl-imidazolidine

A 60° C. solution of 3.0 g (20 mmoles) of d-tartaric acid in 20 ml of ethanol is added in a single portion to a 60° C. solution of 6.15 g (20 mmoles) of racemic 1,3-bis(2',6'-dimethylphenyl)-2-imino-4-methyl-imidazolidine, prepared as described in Example 3, in 50 ml of ethanol. The mixture is allowed to stand at room temperature for 2 days. Thereafter the separated big crystal grains are filtered off, washed with cold ethanol and dried. 5.8 g (63.4%) of the d-tartrate are obtained; m.p.: 186°–189° C., $[\alpha]_D^{20} = +3.5°$ (c=1, in methanol). This salt is recrystallized five times from ethanol to obtain 0.7 g (7.7%) of (+)-1,3-bis(2',6'-dimethylphenyl)-2-imino-4-methyl-imidazolidine-d-tartrate; $[\alpha]_D^{20} = +6.7°$ (c=1, methanol). The majority of the product melts at 181°–182° C., thereafter it crystallizes again upon continued heating, finally it melts at 223°–225° C.

The salt obtained as described above is dissolved in water, the solution is rendered alkaline with 10 n aqueous sodium hydroxide solution, thereafter the separated optically pure dextrorotatory base is filtered off, washed thoroughly with water and dried. The product melts at 122°–124° C.; $[\alpha]_D^{20} = +22.4°$ (c=1, in methanol).

EXAMPLE 85

(+)- and (−)-1,3-Bis(2',6'-dimethylphenyl)-2-imino-4-methyl-imidazolidine

A 60° C. solution of 6.1 g (16.22 mmoles) of dibenzoyl-d-tartaric acid in 150 ml of ethyl acetate is added to a 60° C. solution of 10.0 g (32.53 mmoles) of racemic 1,3-bis(2',6'-dimethylphenyl)-2-imino-4-methyl-imidazolidine, obtained as described in Example 3, in 350 ml of ethyl acetate. The mixture is allowed to stand at room temperature for one week, thereafter the separated crystals are filtered off, washed with ethyl acetate and dried. 8.5 g (39.3%, calculated for the racemic base) of the crude d-tartrate are obtained; m.p.: 117°–119° C., $[\alpha]_D^{20} = +66.1°$ (c=1, in methanol).

This crude substance is dissolved in 100 ml of isopropanol, 500 ml of ethyl acetate are added, and the mixture is allowed to stand at room temperature for 2 days. The separated crystals are filtered off, washed with ethyl acetate and dried. 5.9 g (27.2%) of pure (+)-1,3-bis(2',6'-dimethylphenyl)-2-imino-4-methyl-imidazolidine dibenzoyl-d-tartrate are obtained; m.p.: 123°–125° C., $[\alpha]_D^{20} = +68.4°$ (c=1, in methanol).

The above pure salt is dissolved in 50 ml of methanol, the solution is rendered alkaline with 2 n aqueous sodium hydroxide solution, 300 ml of water are added, and the mixture is allowed to stand at +5° C. overnight. Next day the separated crystals are filtered off, washed with water and dried. 2.2 g (22.0%) of (+)-1,3-bis(2',6'-dimethylphenyl)-2-imino-4-methyl-imidazolidine are obtained; m.p.: 118°–121° C., $[\alpha]_D^{20} = +22.2°$ (c=1, in methanol).

The ethyl acetate mother liquor obtained in the salt formation step is evaporated under reduced pressure, the residue is triturated with dry diethyl ether, and the insolubles are filtered off. The etheral filtrate is evaporated under reduced pressure, and the residue is crystallized from cyclohexane. 0.7 g (7.0%) of (−)-1,3-bis(2',6'-dimethylphenyl)-2-imino-4-methyl-imidazolidine are obtained; m.p.: 119°–120° C., optical purity grade: 81.8%, $[\alpha]_D^{20} = -18.3°$ (c=1, in methanol).

EXAMPLE 86

1,3-Bis(2',6'-dimethylphenyl)-2-acetimino-4-methylene-imidazolidine 0.5 ml of a 2 n methanolic sodium methoxide solution are added to a solution of 0.43 g (1 mmole) of 1,3-bis(2',6'-dimethylphenyl)-2-acetimino-4-bromomethyl-imidazolidine, obtained as described in Example 81, in 10 ml of dry benzene, and the resulting mixture is stirred and boiled for 3 hours. The mixture is cooled, the solvent is evaporated under reduced pressure, and the residue is triturated with water. The insoluble solid is filtered off, washed with water and dried. 0.31 g (89.5%) of 1,3-bis(2',6'-dimethylphenyl)-2-acetimino-4-methylene-imidazolidine are obtained; m.p.: 203°–206° C.

EXAMPLE 87

1,3-Bis(2',6'-dimethylphenyl)-2-imino-4-methyl-imidazolidine fumarate hydrate 3.07 g (0.010 moles) of solid 1,3-bis(2',6'-dimethylphenyl)-2-imino-4-methyl-imidazolidine, obtained as described in Example 3, are added in portions to a stirred solution of 1.28 g (0.011 moles) of fumaric acid in 40 ml of water at 80° to 85° C. The resulting pale yellow solution is decolourized with charcoal and the decolourizing agent is filtered hot. 1,3-Bis(2',6'-dimethylphenyl)-2-imino-4-methyl-imidazolidine fumarate hydrate, containing 2.5 moles of water calculated for the salt, crystallizes from the filtrate upon cooling. The separated crystals are filtered off, washed with icy water and dried. 3.7 g (79.1%) of the aimed compound are obtained. The compound melts first at 85° to 92° C., then it crystallizes again from 130° C. on, and finally melts at 165°–167° C.

EXAMPLE 88

Copper(I)bromide complex of 1,3-bis(2',6'-dimethylphenyl)-2-imino-4-methyl-imidazolidine ($C_{20}H_{25}N_3.0.75$ CuBr)

1.8 g (0.0125 moles) of copper(I)bromide are dissolved in 100 ml of dry acetonitrile under boiling, the insolubles are filtered off, and the resulting clear solution is added dropwise to a stirred and boiled solution of 3.07 g (0.01 moles) of 1,3-bis(2',6'-dimethylphenyl)-2-imino-4-methyl-imidazolidine, prepared as described in Example 3, in 100 ml of dry ethyl acetate. The mixture is stirred and boiled for further 30 minutes, thereafter the resulting green solution is filtered and concentrated to a final volume of about 50 ml. 200 ml of ethyl acetate are added to the concentrate, and the separated crystals are filtered off. 1.9 g of the aimed complex are obtained; m.p.: 255°–257° C.

The filtrate is allowed to stand for 2 days, whereupon further 1.55 g of the complex separate. Thus a total amount of 3.45 g (77%, calculated for the organic base) of the complex is obtained.

EXAMPLE 89

1,3-Bis(2',6'-dimethylphenyl)-2-carbomethoxy-imino-4-methyl-imidazolidine

One proceeds as described in Example 49, with the difference that 1,3-bis(2',6'-dimethylphenyl)-2-imino-4-methyl-imidazolidine, obtained as described in Example 3, and methyl chloroformate are applied as starting substances. The title compound, melting at 141°–142° C., is obtained with a yield of 65.8%.

EXAMPLE 90

1,3-Bis(2',6'-dimethylphenyl)-2-(p-chloro-benzyloxycarbonyl)-imino-4-methyl-imidazolidine One proceeds as described in Example 49, with the difference that 1,3-bis(2',6'-dimethylphenyl)-2-imino-4-methyl-imidazolidine, obtained as described in Example 3, and (p-chloro-benzyl) chloroformate are applied as starting substances. The title compound, melting at 140°–142° C., is obtained with a yield of 13.7%.

The respective 2-(o-chlorobenzyloxycarbonyl)-imino derivative can be similarly prepared.

EXAMPLE 91

1,3-Bis(2',6'-dimethylphenyl)-2-(p-methoxy-benzyloxycarbonyl)-imino-4-methyl-imidazolidine One proceeds as described in Example 49, with the difference that 1,3-bis(2',6'-dimethylphenyl)-2-imino-4-methyl-imidazolidine, obtained as described in Example 3, and (p-methoxy-benzyl) chloroformate are applied as starting substances. The title compound, melting at 135°–137° C., is obtained with a yield of 18.6%.

EXAMPLE 92

1,3-Bis(2',6'-dimethylphenyl)-2-(carbethoxymethyl)-imino-4-methyl-imidazolidine

A solution of 6.14 g (0.02 moles) of 1,3-bis(2',6'-dimethylphenyl)-2-imino-4-methyl-imidazolidine and 2.4 ml (3.6 g, 0.02 moles) of ethyl bromoacetate in 50 ml of dry acetonitrile is boiled for 6 hours. The solvent is evaporated under reduced pressure, the residue is triturated with 30 ml of ethyl acetate, and the separated crystalline crude product is filtered off. 6.2 g of the crude hydrobromide are obtained. This crude product is dissolved in water, the solution is rendered alkaline with concentrated aqueous ammonia, the separated precipitate is filtered off, washed with water and dried. 3.1 g of 1,3-bis(2',6'-dimethylphenyl)-2-(carbethoxymethyl)-imino-4-methyl-imidazolidine, melting at 116°–119° C., are obtained. The product melts at 120°–121.5° C. after recrystallization from cyclohexane.

The aqueous filtrate is rendered alkaline with aqueous sodium hydroxide solution to recover 1.0 g of unreacted starting imino compound. Thus the product is obtained with a yield of 47.1%, calculated for the converted starting substance.

EXAMPLE 93

1,3-Bis(2',6'-dimethylphenyl)-2-carboxymethylimino-4-methyl-imidazolidine 0.4 g (0.001 moles) of 1,3-bis(2',6'-dimethylphenyl)-2-(carbethoxymethyl)-imino-4-methyl-imidazolidine, obtained as described in Example 92, are dissolved in 5 ml of ethanol, and a solution of 0.4 g (0.01 moles) of powdered sodium hydroxide in 5 ml of ethanol is added. The mixture is allowed to stand at room temperature for one hour, thereafter it is poured into water, the aqueous solution is acidified with 1 n aqueous hydrochloric acid, and extracted with chloroform. The chloroform solution is dried over sodium sulfate, and the solvent is evaporated in vacuo. The solid residue is dissolved in 5 ml of isopropanol, the solution is filtered, and 30 ml of dry diethyl ether are added to the clear filtrate. Next day the separated crystals are filtered off, washed with diethyl ether and dried. 0.30 g (82.1%) of 1,3-bis(2',6'-dimethylphenyl)-2-carboxymethylimino-4-methyl-imidazolidine are obtained; m.p.: 307°–310° C.

EXAMPLE 94

1,3-Bis(2',6'-dimethylphenyl)-2-acetimino-4-mercaptomethyl-imidazoline 1.0 g (0.0021 moles) of 1,3-bis(2',6'-dimethylphenyl)-2-acetimino-4-(benzoylmercapto)-methyl-imidazolidine are dissolved in 10 ml of methanol, 1.1 ml of 2 n methanolic sodium methoxide solution are added, and the mixture is stirred at room temperature for 2 days. The mixture is diluted with water and extracted with chloroform. The chloroform solution is washed with water, dried over magnesium sulfate, and the solvent is evaporated. The residue is crystallized from aqueous ethanol to obtain 0.63 g (78.8%) of 1,3-bis(2',6'-dimethylphenyl)-2-acetimino-4-mercaptomethyl-imidazolidine. The compound melts at 208°–210° C. after recrystallization from ethyl acetate.

The S-benzoyl derivative, applied as starting substance, is prepared as follows:

3.5 g (0.0082 moles) of 1,3-bis(2',6'-dimethylphenyl)-2-acetimino-4-bromomethyl-imidazolidine, obtained as described in Example 82, are dissolved in 70 ml of dry acetone, 1.45 g (0.0082 moles) of potassium thiobenzoate and 0.33 g (0.002 moles) of potassium iodide are added, and the mixture is boiled for one hour. The separated inorganic salt is filtered off, and the filtrate is evaporated under reduced pressure. The residue is triturated with cyclohexane, the separated crystals are filtered off, washed with cyclohexane and dried. 3.4 g (85.2%) of 1,3-bis(2',6'-dimethylphenyl)-2-acetimino-4-(benzoylmercapto)-methyl-imidazolidine are obtained; m.p.: 110°–113° C.

EXAMPLE 95

1,3-Bis(2',6'-dimethylphenyl)-2-imino-4-(β-aminoethyl)-imidazolidine

A solution of 2.4 g (0.0068 moles) of 1,3-bis(2',6'-dimethylphenyl)-2-imino-imidazolidine-4-acetamide, obtained as described in Example 77, in 30 ml of dry tetrahydrofuran is added dropwise to a stirred mixture of 10 ml of 1.68 molar borane solution in tetrahydrofuran and 10 ml of dry tetrahydrofuran at a temperature of 5° to 10° C. The resulting mixture is stirred at room temperature for 3 hours and then at the boiling point for 1 hour. The mixture is cooled with ice, 7 ml of 20% aqueous hydrochloric acid are added dropwise, thereafter the solvent is evaporated under reduced pressure. The residue is dissolved in 30 ml of water, the aqueous solution is rendered alkaline with 5 n aqueous sodium hydroxide solution, and the separated crystalline substance is filtered off. 2.0 g (87.0%) of crude 1,3-bis(2',6'-dimethylphenyl)-2-imino-4-(β-aminoethyl)-imidazolidine are obtained. The product melts at 128°–129° C. after recrystallization from diisopropyl ether.

EXAMPLE 96

1,3-Bis(2',6'-dimethylphenyl)-2-imino-4-oxo-imidazolidine 6.3 g (0.0443 moles) of 2,6-dimethylphenyl-cyanamide [m.p.: 120°–122° C.; prepared from 1-(2',6'-dimethylphenyl)-thiourea according to the method of Rathke (Ber. 12, 773 /1879/; Beilstein's Handbuch der organischen Chemie 12 H, 368 /1929/)] are dissolved in 100 ml of dry dimethylformamide, 4.8 g (0.0048 moles) of potassium tert.-butoxide are added, and the mixture is stirred at room temperature for 0.5 hours. Thereafter 8.7 g (0.0443 moles) of N-chloroacetyl-2,6-dimethyl-aniline (m.p.: 145°–146° C.; prepared by acylating 2,6-dimethylaniline with chloroacetyl chloride) are introduced, and the resulting mixture is stirred at 100° C. for 2 hours. The mixture is cooled, poured into water, the separated crystalline product is filtered off, washed with water and dried. This crude product is dissolved in 10% isopropanolic hydrochloric acid, and the salt is precipitated with diethyl ether. 1.7 g (12.5%) of pure 1,3-bis(2',6'-dimethylphenyl)-2-imino-4-oxo-imidazolidine hydrochloride are obtained; m.p.: 219°–221° C.

EXAMPLE 97

1-(1',3'-Bis/2",6"-dimethylphenyl/-4'-methyl-imidazolidine-2'-ylidene)-3-carbethoxy-urea 0.65 ml (0.72 g, 0.00443 moles) of ethyl pyrocarbonate are added to a solution of 1.0 g (0.00285 moles) of 1-(1',3'-bis/2",6"-dimethylphenyl/-4'-methyl-imidazolidine-2'-ylidene)-urea, prepared as described in Example 72, in 10 ml of dry chloroform, and the mixture is allowed to stand at room temperature for 48 hours. Thereafter the solvent and the excess of the reactant are distilled off under reduced pressure. The oily residue is dissolved in 10 ml of diethyl ether, the insolubles are filtered off, and the filtrate is concentrated to a final volume of about 2 ml. Next day the separated crystalline product is filtered off, washed with a small amount of diethyl ether and dried. 0.5 g (41.7%) of 1-(1',3'-bis/2",6"-dimethylphenyl/-4'-methyl-imidazolidine-2'-ylidene)-3-carbethoxy-urea are obtained; m.p.: 123°–125° C.

EXAMPLE 98

1-(1',3'-Bis/2",6"-dimethylphenyl/-4'-methyl-imidazolidine-2'-ylidene)-3-carbethoxy-thiourea 8.3 g (0.085 moles) of potassium rhodanide are reacted with 8.1 ml (9.23 g, 0.085 moles) of ethyl chloroformate as described by Elmore and Ogle (loc. cit.) to form carbethoxy isothiocyanate. This reactant is dissolved in acetone, and a solution of 24.6 g (0.08 moles) of 1,3-bis-(2',6'-dimethylphenyl)-2-imino-4-methyl-imidazolidine, obtained as described in Example 3, in 100 ml of dry acetone is added dropwise to the former solution under stirring at a temperature of 0° to 5° C. The reaction mixture is stirred at 0° to 5° C. for 5 hours, thereafter the solvent is evaporated under reduced pressure, and the oily residue is triturated with isopropanol. The resulting crude crystalline product is recrystallized twice from methanol to obtain 10.0 g (28.5%) of the title compound; m.p.: 99°–101° C.

EXAMPLE 99

1-(1',3'-Bis/2",6"-dimethylphenyl/-4'-methyl-imidazolidine-2'-ylidene)-2-methyl-3-carbethoxy-isothiourea 0.10 ml (0.23 g, 0.0016 moles) of methyl iodide are added to a solution of 0.5 g (0.00114 moles) of 1-(1',3'-bis/2",6"-dimethylphenyl/-4'-methyl-imidazolidine-2'-ylidene)-3-carbethoxy-thiourea, prepared as described in Example 98, in 10 ml of dry dimethylformamide at 0° to 5° C. The resulting mixture is stirred for 0.5 hours at the same temperature, thereafter it is poured onto 100 ml of icy water, and a solution of 0.2 g of potassium hydrogencarbonate in 3 ml of water is added. The separated colourless crystalline substance is filtered off, washed with water and dried. 0.5 g (96.9%) of the title compound are obtained; m.p.: 114°–116° C.

EXAMPLE 100

1-(1',3'-Bis/2'',6''-dimethylphenyl/-4'-methyl-imidazolidine-2'-ylidene)-3-methyl-guanidine A mixture of 1.0 g (0.003 moles) of 1,3-bis(2',6'-dimethylphenyl)-2-cyanimino-4-methyl-imidazolidine, obtained as described in Example 68, and 5.0 g (0.074 moles) of methylamine hydrochloride is heated at 200° to 210° C. in a steel bomb for 8 hours. The mixture is allowed to cool, triturated with 100 ml of water, and the insolubles (0.25 g) are filtered off. The aqueous filtrate is washed with diethyl ether in order to remove the dissolved unreacted starting substance, thereafter the aqueous phase is extracted thrice with 30 ml of chloroform each. The chloroform solutions are combined, dried over anhydrous magnesium sulfate, and the solvent is evaporated under reduced pressure. The resulting crude salt, weighing 0.7 g, is dissolved in tetrahydrofuran, and the pure compound is precipitated with diethyl ether. 0.45 g (41.3%) of 1-(1',3'-bis/2'',6''-dimethylphenyl/-4'-methyl-imidazolidine-2'-ylidene)-3-methylguanidine dihydrochloride are obtained; m.p.: 163°–167° C.

EXAMPLE 101

1,3-Bis(2',6'-dimethylphenyl)-2-($\beta$-hydroxyethyl)-imino-4-methyl-imidazolidine 1.5 ml (1.8 g, 0.022 moles) of ethylene chlorohydrine and 0.35 g (0.002 moles) of potassium iodide are added to a solution of 6.14 g (0.02 moles) of 1,3-bis(2',6'-dimethylphenyl)-2-imino-4-methyl-imidazolidine, obtained as described in Example 3, in 60 ml of dry dimethylformamide. The resulting mixture is stirred at 100° to 105° C. for 6 hours, thereafter it is poured onto 300 ml of icy water. The separated product is filtered off, washed with water and ethyl acetate, and dried. 1.6 g of 1,3-bis(2',6'-dimethylphenyl)-2-($\beta$-hydroxyethyl)-imino-4-methyl-imidazolidine hydrochloride are obtained; m.p.: 288°–291° C. (after recrystallization from a 6:4 mixture of methanol and water).

The aqueous mother liquor obtained in the separation of the crude product is rendered alkaline with aqueous sodium hydroxide solution and then extracted with diethyl ether. In this way 2.0 g of unreacted starting substance are recovered; thus the product is obtained with a yield of 34.3%, calculated for the converted starting substance.

EXAMPLE 102

Tablets

Tablets for oral administration, containing 30 mg of active ingredient, can be prepared e.g. with the following composition:

| | |
|---|---:|
| 1,3-bis(2',6'-dimethylphenyl)-2-imino-4-methyl-imidazolidine fumarate hydrate | 45.7 mg |
| lactose | 44.3 mg |
| potato-starch | 13.0 mg |
| polyvinyl pyrrolidone | 5.0 mg |
| silicium dioxide (colloidal) | 1.0 mg |
| magnesium stearate | 1.0 mg |
| | 110.0 mg |

EXAMPLE 103

Ointments

Ointments for topical application, containing 0.5% of active ingredient, can be prepared e.g. with the following composition:

| | |
|---|---:|
| 1,3-bis(2',6'-dimethylphenyl)-2-imino-4-methyl-imidazolidine fumarate hydrate | 0.76 g |
| distilled water | 72.00 g |
| cetostearyl alcohol (BPO 1973) | 12.00 g |
| polysorbate 60 (BPC 1973) | 4.00 g |
| paraffin oil | 4.00 g |
| vaseline (white) | 2.00 g |
| solution of methyl hydroxybenzoate (Ph. Hg. VI) | 2.00 g |
| distilled water | ad 100.00 g |

What we claim is:

1. A compound of the general formula (I),

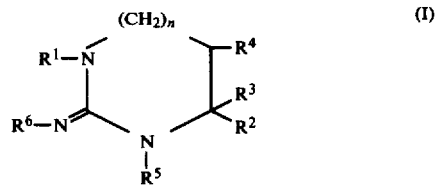

wherein

R$^1$ and R$^5$ each represent a phenyl group optionally substituted with 1 to 3 lower alkoxy, halo, lower alkyl, monohalo-(lower)-alkyl, dihalo-(lower)-alkyl and/or trihalo-(lower) alkyl groups, R$^2$ stands for hydrogen or a lower alkyl group optionally substituted with a hydroxy group or 1 to 3 halogen atoms, R$^3$ and R$^4$ each represent a hydrogen atom or a lower alkyl group, and R$^6$ stands for a carbamoyl, thiocarbamoyl or amidino group having optionally one or two lower alkyl and/or lower alkoxycarbonyl substituents, or a group of the general formula R$^7$—CO-wherein R$^7$ stands for a lower alkoxy group, an aryloxy group, an aralkoxy group and n is equal to 0, with the proviso that when R$^1$ and R$^5$ each represent a phenyl group, R$^2$ and R$^3$ may not stand for hydrogen or a pharmaceutically acceptable acid addition salt, a pure isomer or an isomeric mixture thereof.

2. 1,3-Bis(2',6'-dimethylphenyl)-2-carbethoxy-imino-4 methyl-imidazolidine.

3. 1,3-Bis(2',6'-dimethylphenyl)-2-(p-methoxy-benzyloxy-carbonyl)-imino-4-methyl-imidazolidine.

4. 1-[1',3'-Bis(2'',6''-dimethylphenyl)-4'-methyl-imidazolidin-2'-ylidene]-3-carbethoxy-thiourea.

* * * * *